United States Patent
Gauilliere et al.

(10) Patent No.: US 12,352,765 B2
(45) Date of Patent: Jul. 8, 2025

(54) COMPOSITIONS AND METHODS OF PROGNOSIS AND CLASSIFICATION FOR PREECLAMPSIA

(71) Applicant: The Board of Trustees of the Leland Stanford Junior University, Stanford, CA (US)

(72) Inventors: Brice L. Gauilliere, Palo Alto, CA (US); Martin S. Angst, Stanford, CA (US); Nima Aghaeepour, Stanford, CA (US); David K. Stevenson, Palo Alto, CA (US); Xiaoyuan Han, Stanford, CA (US); Mohammad S. Ghaemi, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1040 days.

(21) Appl. No.: 17/291,858

(22) PCT Filed: Nov. 14, 2019

(86) PCT No.: PCT/US2019/061504
§ 371 (c)(1),
(2) Date: May 6, 2021

(87) PCT Pub. No.: WO2020/102556
PCT Pub. Date: May 22, 2020

(65) Prior Publication Data
US 2022/0011319 A1    Jan. 13, 2022

Related U.S. Application Data

(60) Provisional application No. 62/767,957, filed on Nov. 15, 2018.

(51) Int. Cl.
*G01N 33/68* (2006.01)
(52) U.S. Cl.
CPC ..... *G01N 33/6893* (2013.01); *G01N 2333/46* (2013.01); *G01N 2800/368* (2013.01)
(58) Field of Classification Search
None
See application file for complete search history.

(56) References Cited

U.S. PATENT DOCUMENTS

2009/0117588 A1    5/2009    Karumanchi et al.
2010/0015639 A1    1/2010    Patankar et al.
2013/0071860 A1    3/2013    Hale et al.

OTHER PUBLICATIONS

Mcaleer, Author Manuscript of Crit Rev Immunol. 2008; 28(4): 281-299 (Year: 2008).*
Spitzer, Cell, 2016; 165: 780-791 (Year: 2016).*
Zhang et al., J Mol Hist (2015) 46:205-219 (Year: 2015).*
Chiasson et al. (2011) "Fk506 Binding Protein 12 Deficiency in Endothelial and Hematopoietic Cells Decreases Regulatory T Cells and Causes Hypertension" vol. 57, Issue 6, pp. 1167-1175.
Aghaeepour et al., (2017) "An immune clock of human pregnancy", Science Immunology, 2:15, pp. 1-12.
Bersinger et al. (2009) "Serum markers for pre—eclampsia: An update on the analytes to be determined in the first, second, and Noa FELDS, third trimester", Immuno-analyse et biologie spécialisée, 24:2, pp. 58-68.
Gergely et al., (2010) "Decreased No. of FoxP3+ regulatory T cells in preeclampsia", ACTA Obstetricia and Gynecologica Scandinavica, 87:11, pp. 1229-1233.
Han et al. (2019) "Differential Dynamics of the Maternal Immune System in Healthy Pregnancy and Preeclampsia", Frontiers in Immunology, vol. 10:1305 1305.
Han et al., (2019) "Supplementary Material: Differential Dynamics of the Maternal Immune System in Healthy Pregnancy and Preeclampsia", Frontiers in Immunology, vol. 10, pp. 1-6.
Santner-Nanan et al., (2009) "Systemic Increase in the Ratio between Foxp3 + and IL-17-Producing CD4 + T Cells in Healthy Pregnancy but Not in Preeclampsia", The Journal of Immunology, 183:11, pp. 7023-7030.

* cited by examiner

*Primary Examiner* — Christina M Borgeest
(74) *Attorney, Agent, or Firm* — Pamela J. Sherwood; Bozicevic, Field & Francis LLP

(57) ABSTRACT

Multiparametric analysis is performed at the single cell level of biological samples obtained from an individual during pregnancy to obtain a determination of changes in immune cell subsets, which changes include, without limitation, altered activation states of proteins involved in signaling pathways. Changes occur in signaling pathways of these immune cells that are predictive of propensity to develop preeclampsia in the pregnancy.

19 Claims, 11 Drawing Sheets

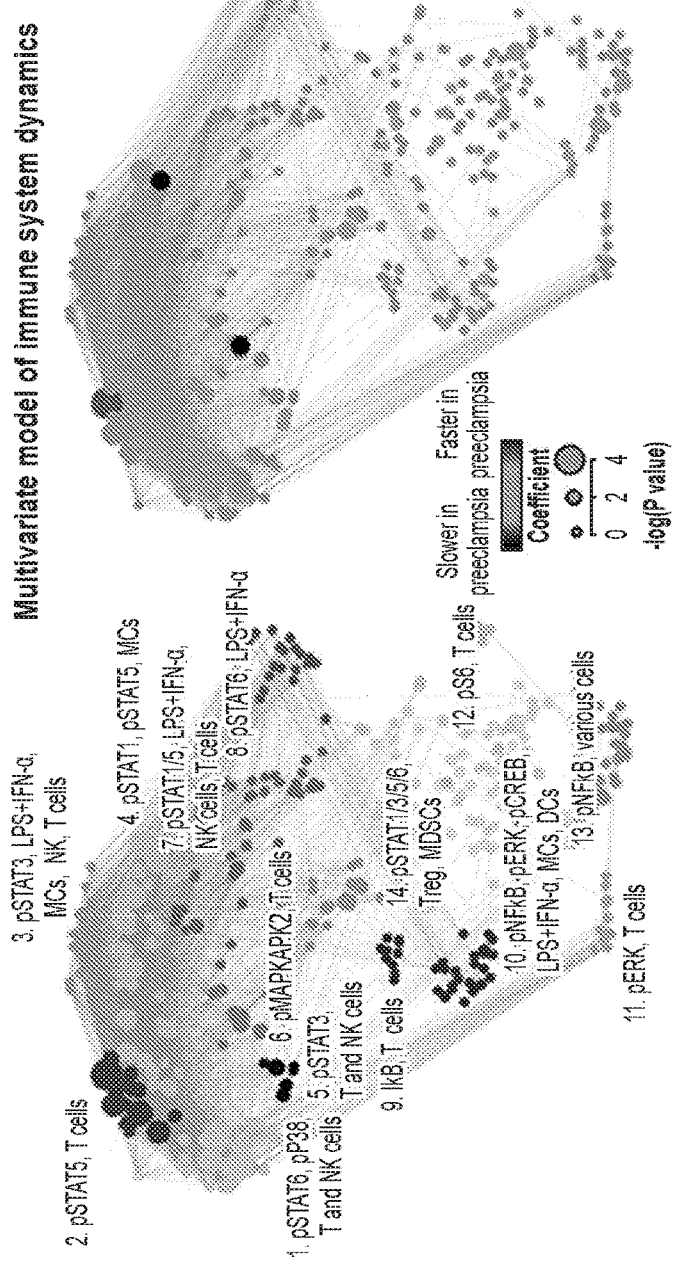
FIG. 2A
FIG. 2B
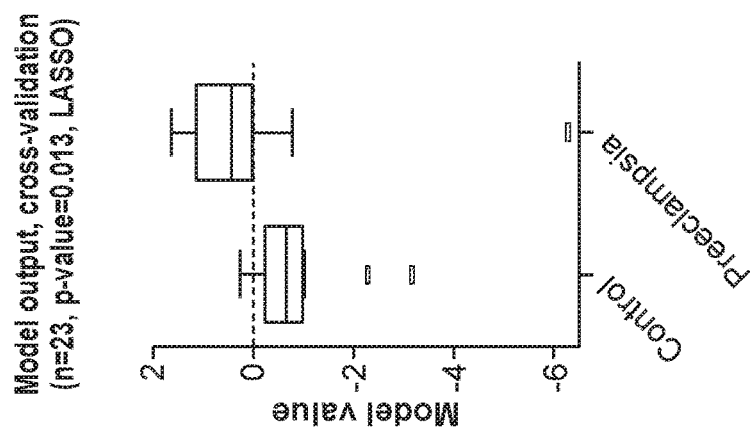
FIG. 2C

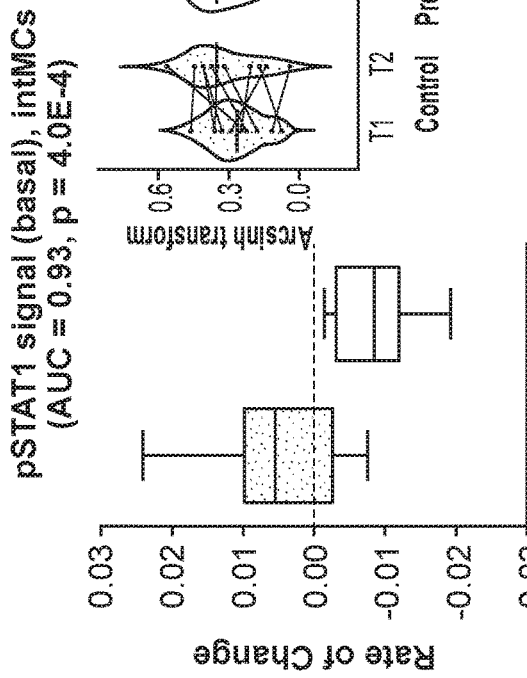
FIG. 4A
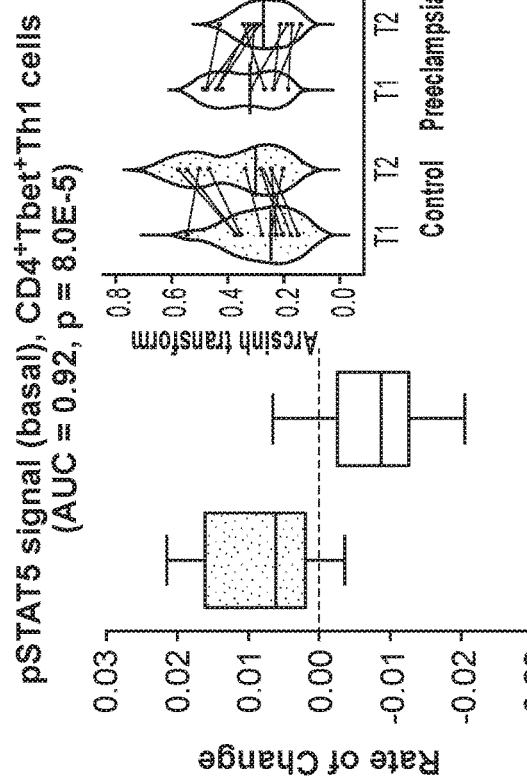
FIG. 4B
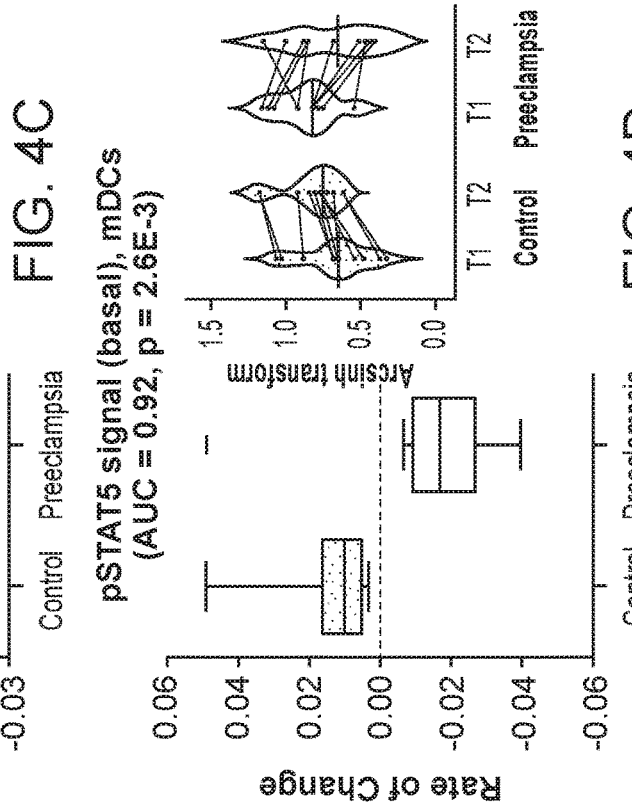
FIG. 4C
FIG. 4D

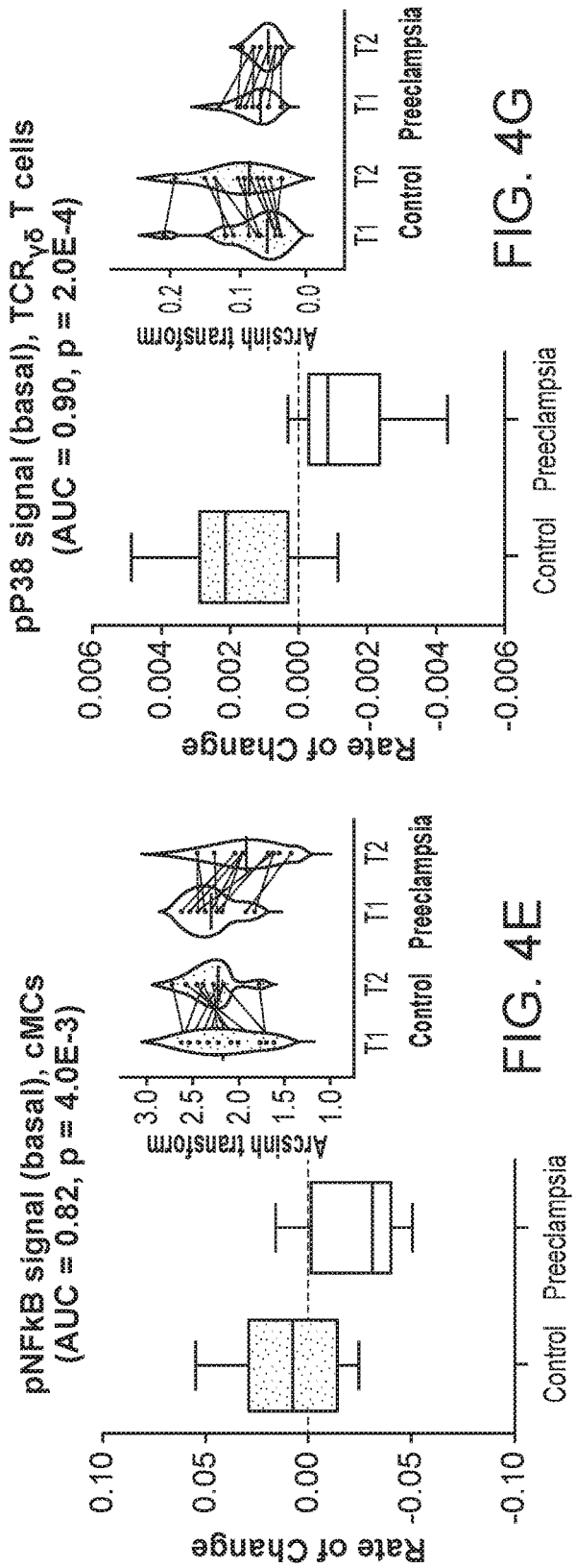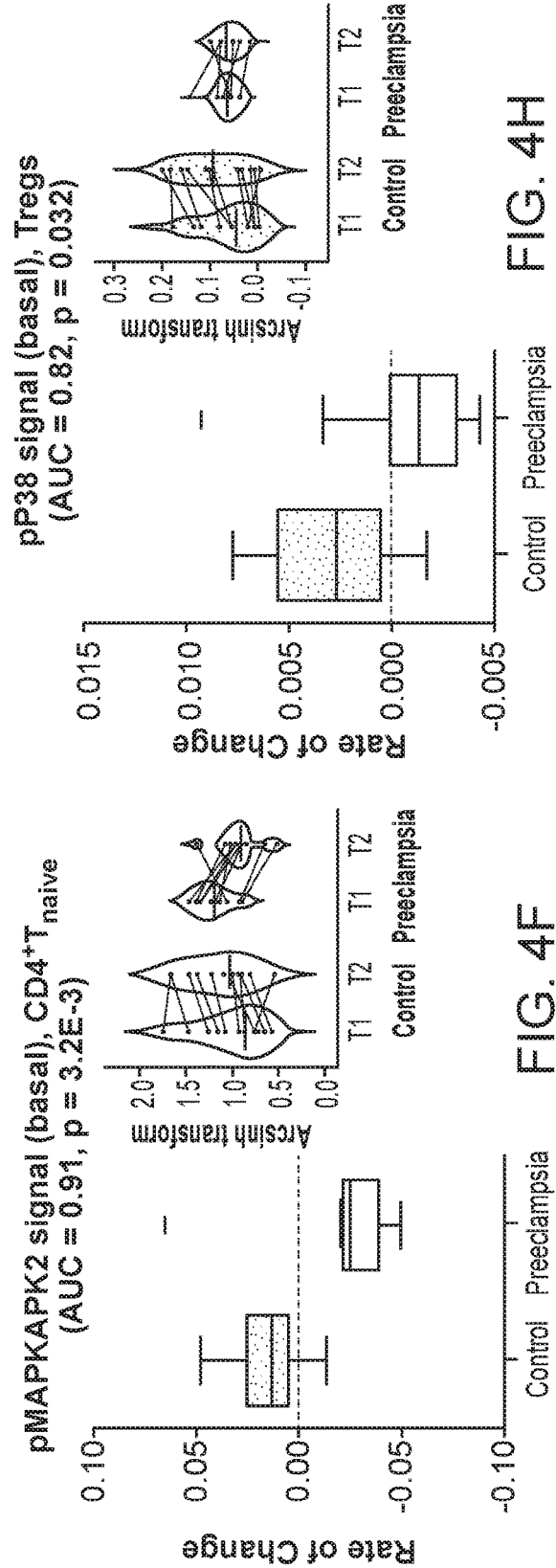
FIG. 4E
FIG. 4F
FIG. 4G
FIG. 4H

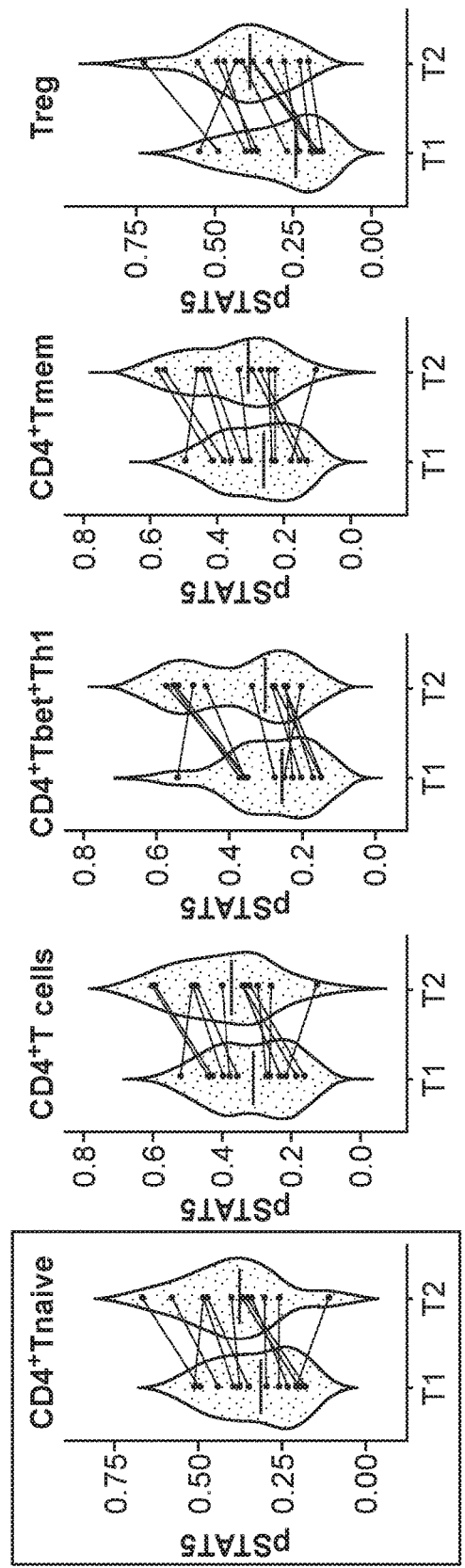
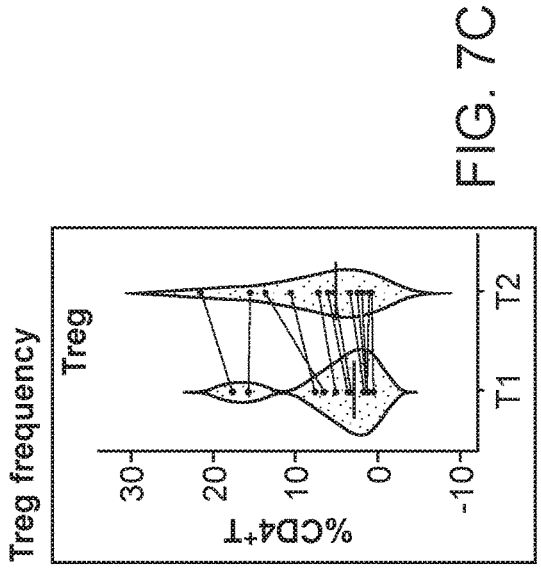
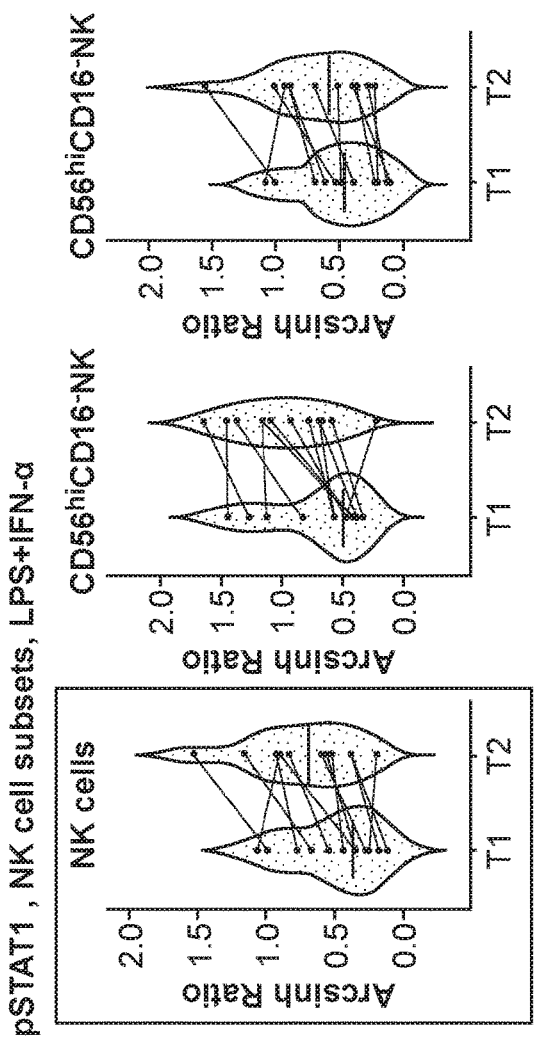
FIG. 7A
FIG. 7C
FIG. 7B

COMPOSITIONS AND METHODS OF PROGNOSIS AND CLASSIFICATION FOR PREECLAMPSIA

CROSS-REFERENCE TO RELATED APPLICATIONS

This application claims priority to U.S. Ser. No. 62/767,957 filed Nov. 15, 2018, the contents of each of which is incorporated herein by reference.

BACKGROUND OF THE INVENTION

Preeclampsia is a severe complication of pregnancy defined by the new onset of hypertension and signs of maternal organ dysfunction after the 20th week of gestation. Preeclampsia affects between 2 and 8% of all pregnant women—over 8 million women per year worldwide—and is a leading cause of maternal deaths (9-26%). Preeclampsia also accounts for significant neonatal morbidity and mortality due to intrauterine growth restriction, intrauterine fetal demise, and preterm delivery. However, no diagnostic test reliably detects preeclampsia early in its development, so treatment can be started only after the onset of signs and symptoms, at which point irreparable harm to the mother and fetus may already have occurred.

Preeclampsia is a multisystem disorder characterized by placental and endothelial dysfunction, leading to hypertension and other end-organ damage such as impaired kidney, liver, neurological or hematological function. Well-described placental abnormalities, including in trophoblast invasion and uterine spiral artery formation, suggest that the roots of preeclampsia are established in the first weeks of pregnancy, before the development of signs and symptoms. While markers of placental and endothelial dysfunction—such as increases in soluble FMS-like tyrosine kinase 1 (sFLT-1) levels, and decreases in vascular endothelial growth factor (VEGF) and placental growth factor (PLGF) levels—can be valuable clinically in ruling out suspected preeclampsia, early diagnosis of preeclampsia remains clinically challenging.

The present disclosure addresses this issue.

SUMMARY OF THE INVENTION

Compositions and methods are provided for classification, diagnosis, prognosis, theranosis, and/or prediction of an outcome during pregnancy in a subject with respect to development of preeclampsia.

In some embodiments a high-dimensional mass cytometry, or fluorescence-based flow cytometry immunoassay is used to characterize the dynamic changes in immune cell features, which may include cell distribution and functional responses, in maternal blood during pregnancy. Analysis may be performed as early as the first trimester of pregnancy, for example after about 11 gestational weeks, after about 12 gestational weeks, after about 13 gestational weeks, after about 14 gestational weeks, and usually before full term, e.g. prior to about 40 gestational weeks, prior to about 35 gestational weeks, prior to about 30 gestational weeks, prior to about 25 gestational weeks, prior to about 20 gestational weeks. As discussed herein, change over time in immune cell features can be an important indicator, e.g. with 2, 3, 4, 5 or more different time points for assessment, which time points may be 2, 3, 4, 5, 6, 7, 8, 9, 10, 11, 12, 13, 14, 15, or more weeks apart, for example with a sample taken in the first and in the second trimester. Analysis is optionally performed with a mass cytometry immunoassay or flow cytometry immunoassay for an in-depth assessment of the dynamics of the peripheral immune system during pregnancy.

It is shown herein that measurement of one or more cell-specific immune features can accurately identify a patient at high risk of preeclampsia at a stage of pregnancy early enough for intervention, and well ahead of current clinical diagnosis of preeclampsia. These immune features include, for example, elevated pro-inflammatory innate immune responses early in pregnancy, and impaired regulatory T (Treg) cell signaling. The cells are fixed and stained with antibodies suitable for flow cytometry or mass cytometry analysis. An immune feature of particular interest is the change in the basal level of phosphorylated STAT5 protein (pSTAT5) in $CD4^+$ T cells, measured in at least two different time points. The time points may be 2, 3, 4, 5, 6, 7, 8, 9, 10, 11, 12, 13, 14, 15, or more weeks apart, for example with a sample taken in the first and in the second trimester. The analysis may be gated on $CD4^+$ T cells or subsets of CD4+ T cells, including without limitation $Tbet^+$ T cells, $CD25^+$ T cells, etc. A decrease in the level of pSTAT5 in these cells over the course of the first two trimesters is indicative of a predisposition to develop preeclampsia. This analysis can be combined with analysis of additional immune features, as described below.

A significant change in an immune feature between two time points can be a rate of change of from about |0.01|, |0.02|, up to |0.05|, where a decreasing value will be, for example, −0.01, −0.02, −0.05, etc., where the time points are from 2-4 months apart, and can be around 3 months (one trimester) apart.

Individuals showing immune features indicative of preeclampsia can be treated accordingly. Because the diagnosis can be provided significantly before clinical symptoms of preeclampsia, the methods herein provide a means of timely intervention. Intervention can include monitoring blood pressure at regular, e.g. daily, intervals. Low-dose aspirin, e.g. a dose of about 81 mg per day may be prescribed after about 12 weeks gestation. Individuals may also be treated with a low dose of IL-2 to restore STAT5 signaling in T cells, including Treg cells.

Immune features for analysis may be selected from the following, where the change in the feature indicative of preeclampsia development is assessed over at least two time points as indicated above: decreased pSTAT5 (basal) in $CD4^+$ T cells; decreased pMAPKAPK2 (basal) in $CD4^+$ T naive cells; decreased pSTAT5 (basal) in mDCs; decreased pSTAT1 (basal) in cMCs; decreased pNFκB (basal) in cMCs; decreased pP38 (basal) in Treg cells; decreased pSTAT1 (basal) in intMC; and decreased pP38 (basal) in γδ T cells.

In one embodiment, analysis of pSTAT5 (basal) in $CD4^+$ T cells is combined with one or more of decreased pMAPKAPK2 (basal) in $CD4^+$ T naive cells; decreased pSTAT5 (basal) in mDCs; decreased pSTAT1 (basal) in cMCs; decreased pNFκB (basal) in cMCs; decreased pP38 (basal) in Treg cells; decreased pSTAT1 (basal) in intMC; and decreased pP38 (basal) in γδ T cells. In such an embodiment, the markers for analysis may comprise an affinity reagent, such as an antibody, specific for CD4, and an affinity reagent, such as an antibody, specific for pSTAT5. The markers are optionally combined with additional affinity reagents for further immune cell subsets.

For example, peripheral blood mononuclear cells (PBMCs) or whole blood samples collected longitudinally during pregnancy are analyzed using a multi-parameter immunoassay for an in-depth profiling of peripheral immune cell adaptations. For each patient sample, a plurality of immune features are quantified on a per cell basis in multiple distinct innate and adaptive immune cell subsets (shown in FIG. 1). Immune features included cell frequencies and the activity (e.g. phosphorylation state) of intracellular signaling proteins measured at baseline (basal signaling activity). Preferred immune features as indicated above are basal levels of signaling proteins in defined subsets of immune cells. Communities of immune feature characteristics are determined. To parameterize the dynamic changes in the peripheral immune system during pregnancy, the rate of change between the first and second sampling time points is also calculated for each immune feature.

The predictive analysis identified a multivariate model that accurately differentiates women who develop preeclampsia from controls. Most of the informative immune features are intracellular signaling responses. Eight immune features are highly significant as predictors of preeclampsia after controlling for demographic and clinical variables, for example as shown in FIG. 3B.

In some embodiments, a patient is analyzed for change in pSTAT5 signal (basal) in CD4+Tbet+Th1 cells between the first and second trimester. The pSTAT5 signal increases consistently in Th1 cells between the first and second trimesters in the control group, but decreases in women who develop preeclampsia. The abnormal pSTAT5 dynamics are shared among several T cell subsets including $CD4^+$ T naive cells and $CD25^+FoxP3^+$ Tregs. Patients with decreasing measurement of pSTAT5 signal in T cells, particularly $CD4^+$ T cells, may be treated accordingly with monitoring, regular measurement of blood pressure, low dose aspirin, low dose IL-2, and the like as appropriate for treatment of preeclampsia.

Additional immune features show that overall, strong pro-inflammatory cell responses early during pregnancy alter the immunologic trajectory of women who went on to develop preeclampsia. In innate immune compartments, the pSTAT1, pSTAT5, and pNFκB signals (basal) are elevated in intermediate monocytes (intMCs), myeloid dendritic cells (mDCs), and classical monocytes (cMCs), respectively, during the first trimester in preeclamptic women compared with controls. These responses gradually decreased during preeclamptic pregnancies, but increased in the control group. In adaptive immune compartments, elevated pro-inflammatory signaling responses in Th1 cells (pSTAT5) during the first trimester of pregnancy were coupled with abnormal signaling dynamics in $CD4^+$T naïve cells, $TCR_{\gamma\delta}$ and $CD25^+$ $FoxP3^+$Tregs. The pP38 signal, which is required for Treg suppressive function, increased in Tregs during pregnancy in controls but not in women with preeclampsia.

In one embodiment of the invention, the methods of determining propensity to develop preeclampsia in a patient during pregnancy comprises obtaining a patient sample(s) comprising circulating immune cells. Blood samples are a convenient source of circulating immune cells, particularly whole blood, although PBMC fractions also find use. The patient sample is optionally stimulated ex vivo with an effective dose of an agent that stimulates pSTAT5, e.g. IFNα, or IL-2 although as shown herein basal levels can be sufficiently informative. The sample(s) is physically contacted with a panel of affinity reagents specific for signaling proteins and for markers that distinguish subsets of immune cells. Usually the affinity reagents comprise a detectable label, e.g. isotope, fluorophore, etc. Signal intensity of the markers is measured, preferably at a single cell level. Suitable methods of analysis include, without limitation, flow cytometry, mass cytometry, confocal microscopy, and the like. The data, which can include measurements of intensity of signaling molecules and changes in phosphorylation in selected immune cell subsets, etc., is compared to measurements of the same from the baseline cell population. The data can be normalized for comparison.

In other embodiments of the invention a device or kit is provided for the analysis of patient samples. Such devices or kits will include reagents that specifically identify one or more cells and signaling proteins indicative of the status of the patient, including without limitation affinity reagents. The reagents can be provided in isolated form, or pre-mixed as a cocktail suitable for the methods of the invention. A kit can include instructions for using the plurality of reagents to determine data from the sample; and instructions for statistically analyzing the data. The kits may be provided in combination with a system for analysis, e.g. a system implemented on a computer. Such a system may include a software component configured for analysis of data obtained by the methods of the invention.

Also described herein is a method for assessing prognosis for preeclampsia during pregnancy, comprising: obtaining a dataset associated with a sample obtained from the subject, wherein the dataset comprises quantitative data for specific immune cell subset; and analyzing the dataset for changes at the single cell level for these markers, wherein a statistically significant match with a preeclampsia pattern is indicative of the prognosis to develop preeclampsia. The data may be analyzed by a computer processor. The processor may be communicatively coupled to a storage memory for analyzing the data. Also described herein is a computer-readable storage medium storing computer-executable program code, the program code comprising: program code for storing and analyzing data obtained by the methods of the invention.

In an embodiment, the method further comprises selecting a treatment regimen for the patient based on the analysis. In an embodiment, the method further comprises determining a treatment course for the subject based on the analysis. Treatment regimens of interest can include decision-making for proceeding with extended hospital stay, medication for hypertension, blood-pressure monitoring, low dose aspirin, low dose IL-2, extended care at an intermediate facility, increased follow-up, and the like.

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 2A-2C. Predictive modeling of immune response dynamics associated with preeclampsia. (FIG. 2A) The correlation network segregates into 14 communities of correlated immune features evolving in synchrony during pregnancy. The communities were annotated on the basis of immune feature characteristics (signaling property, stimulation, or cell subset) most commonly represented within each community. (FIG. 2B) A predictive multivariate model built on immune feature dynamics (rate of change between the first and second time points). LASSO identified patients that develop preeclampsia within 12-14 weeks after the last sampling time. Red/blue dots highlight immune features that evolve faster/slower in preeclampsia compared to Control. Dot size indicates the $-\log_{10}$ of p-value of model components compared between preeclamptic women and controls (Student t test). (FIG. 2C) Boxplots showing model prediction for controls and preeclamptic women (AUC 0.803, cross-validation p-value=0.013).

(FIG. 3A) The bar graph depicts the frequency of immune feature selection across all cross-validation iterations. Blue line indicates piecewise regression fit for identification of a breakpoint indicating ten immune features that are most informative to the multivariate LASSO model. (FIG. 3B) The most informative immune features and their respective immunological communities are highlighted on the correlation network.

FIG. 4A-4H. Model components reveals disrupted innate and adaptive immune cell dynamics in preeclampsia. Boxplots (FIG. 4A-4D) depict the rate of change of indicated immune feature for the eighth most informative model components. AUC and p-values are indicated on each graph (ROC analysis). Insets (FIG. 4E-4H) depict immune feature values (arcsinh transform of the mass cytometry intracellular signal mean intensity) at individual time points (T1, T2) and for each patient. Color code: purple=controls, orange=preeclampsia.

FIG. 7A-7C. The mass cytometry immunoassay detects expected immune cell adaptations during a healthy pregnancy. Targeted analysis of select immune adaptations in the control group confirms previously reported signaling and frequency immune cell adaptations during a normal pregnancy, including (FIG. 7A) increased basal pSTAT5 signals in CD4$^+$T naive (p=0.015), CD4$^+$Tmem (p=0.013) and Treg cell subsets (p=0.008), (FIG. 7B) increased pSTAT1 response to LPS+IFN-α in NK cell subsets (p=0.004) and (FIG. 7C) increased Treg cell frequency (p=0.008).

DETAILED DESCRIPTION

Figure 1:
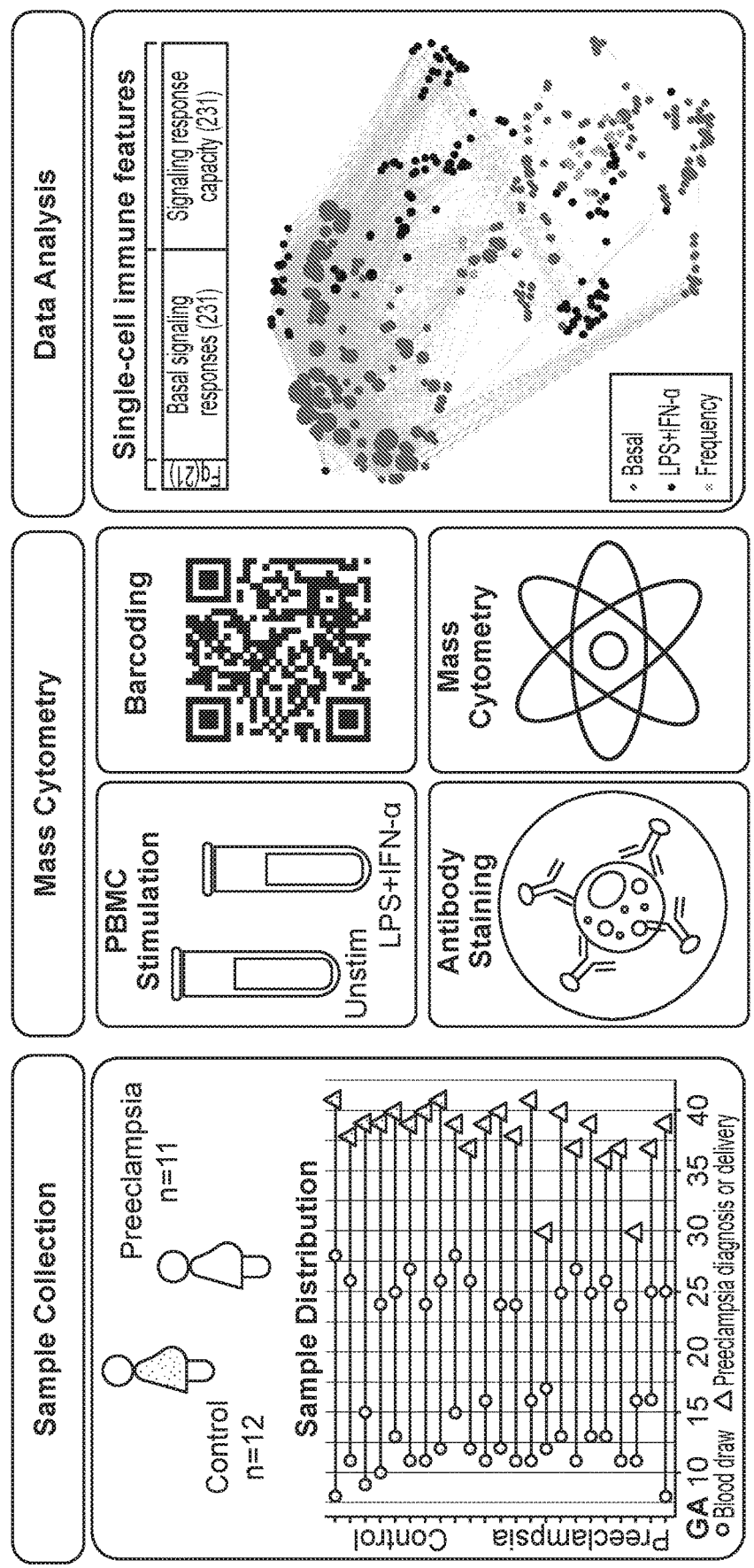
FIG. 1. Experimental workflow for the deep profiling of immune system dynamics in preeclampsia. Eleven women with preeclampsia and 12 healthy (normotensive) women were studied. PBMCs were obtained at two time points during the first 28 weeks of pregnancy. Sample collection time (dots), preeclampsia diagnosis (orange triangles), or delivery (purple triangles) are indicated for individual preeclamptic patients (orange lines) and controls (purple lines). PBMCs were either left unstimulated or stimulated with a cocktail of LPS and IFN-α. Immune cells were barcoded, stained with surface and intracellular antibodies and analyzed with mass cytometry. The assay produced three categories of immune features, providing information about cell frequency (Fq) measured in 21 immune cell subsets (blue bar), basal intracellular signaling activity (green bar), and cell type-specific signaling capacity in response to stimulation with LPS and IFN-α (red bar). The number of immune features contained within each data category is indicated in parentheses. Correlation network reveals the relationships between immune features within and across mass cytometry data categories. A correlation network highlights the relationship between measured immune features (Spearman's coefficient).

These and other features of the present teachings will become more apparent from the description herein. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Most of the words used in this specification have the meaning that would be attributed to those words by one skilled in the art. Words specifically defined in the specification have the meaning provided in the context of the present teachings as a whole, and as are typically understood by those skilled in the art. In the event that a conflict arises between an art-understood definition of a word or phrase and a definition of the word or phrase as specifically taught in this specification, the specification shall control.

It must be noted that, as used in the specification and the appended claims, the singular forms "a," "an," and "the" include plural referents unless the context clearly dictates otherwise.

Compositions and methods are provided for prognostic classification of patients during pregnancy according to their propensity to develop preeclampsia, using an analysis at the single cell level of activation of signaling pathways in specific immune cell subsets. Patterns of response are obtained by quantitating specific activated signal proteins in immune cell subsets of interest, for a period of time during pregnancy, usually for at least two timepoints during pregnancy. The pattern of response is indicative of the patient's propensity to develop preeclampsia. Once a classification or prognosis has been made, it can be provided to a patient or caregiver. The classification can provide prognostic information to guide clinical decision making, both in terms of institution of and escalation of treatment, and in some cases may further include selection of a therapeutic agent or regimen.

The information obtained from the signaling protein patterns of response can be used to (a) determine type and level of therapeutic intervention warranted and (b) to optimize the selection of therapeutic agents. With this approach, therapeutic regimens can be individualized and tailored according to the propensity to develop preeclampsia, thereby providing a regimen that is individually appropriate.

The terms "subject," "individual," and "patient" are used interchangeably herein to refer to a vertebrate, preferably a mammal, more preferably a human. Mammalian species that provide samples for analysis include canines; felines;

equines; bovines; ovines; etc. and primates, particularly humans. Animal models, particularly small mammals, e.g. murine, lagomorpha, etc. can be used for experimental investigations. The methods of the invention can be applied for veterinary purposes.

As used herein, the term "theranosis" refers to the use of results obtained from a diagnostic method to direct the selection of, maintenance of, or changes to a therapeutic regimen, including but not limited to the choice of one or more therapeutic agents, changes in dose level, changes in dose schedule, changes in mode of administration, and changes in formulation. Diagnostic methods used to inform a theranosis can include any that provides information on the state of a disease, condition, or symptom.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "therapeutically effective amount" refers to the amount of an agent that is sufficient to effect beneficial or desired results. The therapeutically effective amount will vary depending upon the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose will vary depending on the particular agent chosen, the dosing regimen to be followed, whether it is administered in combination with other compounds, timing of administration, the tissue to be imaged, and the physical delivery system in which it is carried.

"Suitable conditions" shall have a meaning dependent on the context in which this term is used. That is, when used in connection with an antibody, the term shall mean conditions that permit an antibody to bind to its corresponding antigen. When used in connection with contacting an agent to a cell, this term shall mean conditions that permit an agent capable of doing so to enter a cell and perform its intended function. In one embodiment, the term "suitable conditions" as used herein means physiological conditions.

The term "inflammatory" response is the development of a humoral (antibody mediated) and/or a cellular response, which cellular response may be mediated by antigen-specific T cells or their secretion products), and innate immune cells. An "immunogen" is capable of inducing an immunological response against itself on administration to a mammal or due to autoimmune disease.

The terms "biomarker," "biomarkers," "marker" or "markers" for the purposes of the invention refer to, without limitation, proteins together with their related metabolites, mutations, variants, polymorphisms, modifications, fragments, subunits, degradation products, elements, and other analytes or sample-derived measures. Markers can include expression levels of an intracellular protein or extracellular protein. Markers can also include combinations of any one or more of the foregoing measurements, including temporal trends and differences. Broadly used, a marker can also refer to an immune cell subset.

To "analyze" includes determining a set of values associated with a sample by measurement of a marker (such as, e.g., presence or absence of a marker or constituent expression levels) in the sample and comparing the measurement against measurement in a sample or set of samples from the same subject or other control subject(s). The markers of the present teachings can be analyzed by any of various conventional methods known in the art. To "analyze" can include performing a statistical analysis, e.g. normalization of data, determination of statistical significance, determination of statistical correlations, clustering algorithms, and the like.

A "sample" in the context of the present teachings refers to any biological sample that is isolated from a subject, generally a sample comprising circulating immune cells. A sample can include, without limitation, an aliquot of body fluid, whole blood, PBMC (white blood cells or leucocytes), tissue biopsies, synovial fluid, lymphatic fluid, ascites fluid, and interstitial or extracellular fluid. "Blood sample" can refer to whole blood or a fraction thereof, including blood cells, white blood cells or leucocytes. Samples can be obtained from a subject by means including but not limited to venipuncture, biopsy, needle aspirate, lavage, scraping, surgical incision, or intervention or other means known in the art.

Optionally samples are activated ex vivo, which as used herein refers to the contacting of a sample, e.g. a blood sample or cells derived therefrom, outside of the body with a stimulating agent. In some embodiments whole blood is preferred. The sample may be diluted or suspended in a suitable medium that maintains the viability of the cells, e.g. minimal media, PBS, etc. The sample can be fresh or frozen. Stimulating agents of interest include those agents that activate T cells, e.g. LPS (1 µg/mL) and/or IFN-α (100 ng/mL). Generally the activation of cells ex vivo is compared to a negative control, e.g. medium only, or an agent that does not elicit activation. The cells are incubated for a period of time sufficient for activation. For example, the time for action can be up to about 1 hour, up to about 45 minutes, up to about 30 minutes, up to about 15 minutes, and may be up to about 10 minutes or up to about 5 minutes. In some embodiments the period of time is up to about 24 hours. Following activation, the cells are fixed for analysis.

A "dataset" is a set of numerical values resulting from evaluation of a sample (or population of samples) under a desired condition. The values of the dataset can be obtained, for example, by experimentally obtaining measures from a sample and constructing a dataset from these measurements; or alternatively, by obtaining a dataset from a service provider such as a laboratory, or from a database or a server on which the dataset has been stored. Similarly, the term "obtaining a dataset associated with a sample" encompasses obtaining a set of data determined from at least one sample. Obtaining a dataset encompasses obtaining a sample, and processing the sample to experimentally determine the data, e.g., via measuring antibody binding, or other methods of quantitating a signaling response. The phrase also encompasses receiving a set of data, e.g., from a third party that has processed the sample to experimentally determine the dataset.

"Measuring" or "measurement" in the context of the present teachings refers to determining the presence, absence, quantity, amount, or effective amount of a substance in a clinical or subject-derived sample, including the presence, absence, or concentration levels of such substances, and/or evaluating the values or categorization of a subject's clinical parameters based on a control, e.g. baseline levels of the marker.

Classification can be made according to predictive modeling methods that set a threshold for determining the probability that a sample belongs to a given class. The probability preferably is at least 50%, or at least 60% or at least 70% or at least 80% or higher. Classifications also can be made by determining whether a comparison between an obtained dataset and a reference dataset yields a statistically significant difference. If so, then the sample from which the dataset was obtained is classified as not belonging to the reference dataset class. Conversely, if such a comparison is not statistically significantly different from the reference dataset, then the sample from which the dataset was obtained is classified as belonging to the reference dataset class.

The predictive ability of a model can be evaluated according to its ability to provide a quality metric, e.g. AUC or accuracy, of a particular value, or range of values. In some embodiments, a desired quality threshold is a predictive model that will classify a sample with an accuracy of at least about 0.7, at least about 0.75, at least about 0.8, at least about 0.85, at least about 0.9, at least about 0.95, or higher. As an alternative measure, a desired quality threshold can refer to a predictive model that will classify a sample with an AUC (area under the curve) of at least about 0.7, at least about 0.75, at least about 0.8, at least about 0.85, at least about 0.9, or higher.

As is known in the art, the relative sensitivity and specificity of a predictive model can be "tuned" to favor either the selectivity metric or the sensitivity metric, where the two metrics have an inverse relationship. The limits in a model as described above can be adjusted to provide a selected sensitivity or specificity level, depending on the particular requirements of the test being performed. One or both of sensitivity and specificity can be at least about at least about 0.7, at least about 0.75, at least about 0.8, at least about 0.85, at least about 0.9, or higher.

"Affinity reagent", or "specific binding member" may be used to refer to an affinity reagent, such as an antibody, ligand, etc. that selectively binds to a protein or marker of the invention. The term "affinity reagent" includes any molecule, e.g., peptide, nucleic acid, small organic molecule. For some purposes, an affinity reagent selectively binds to a cell surface marker, e.g. CD3, CD14, CD66, HLA-DR, CD11 b, CD33, CD45, CD235, CD61, CD19, CD4, CD8, CD123, CCR7, and the like. For other purposes an affinity reagent selectively binds to a cellular signaling protein, particularly one which is capable of detecting an activation state of a signaling protein over another activation state of the signaling protein. Signaling proteins of interest include, without limitation, pSTAT3, pSTAT1, pCREB, pSTAT6, pPLCγ2, pSTAT5, pSTAT4, pERK, pP38, prpS6, pNF-κB (p65), pMAPKAPK2, pP90RSK, etc.

In some embodiments, the affinity reagent is a peptide, polypeptide, oligopeptide or a protein, particularly antibodies and specific binding fragments and variants thereof. The peptide, polypeptide, oligopeptide or protein can be made up of naturally occurring amino acids and peptide bonds, or synthetic peptidomimetic structures. Thus "amino acid", or "peptide residue", as used herein include both naturally occurring and synthetic amino acids. Proteins including non-naturally occurring amino acids can be synthesized or in some cases, made recombinantly; see van Hest et al., FEBS Lett 428:(I-2) 68-70 May 22, 1998 and Tang et al., Abstr. Pap Am. Chem. S218: U138 Part 2 Aug. 22, 1999, both of which are expressly incorporated by reference herein.

Methods of the present invention can be used to detect any particular signaling protein in a sample that is antigenically detectable and antigenically distinguishable from other signaling proteins which are present in the sample. For example, activation state-specific antibodies can be used to identify distinct signaling cascades of a subset or subpopulation of complex cell populations; and the ordering of protein activation (e.g., kinase activation) in potential signaling hierarchies. Hence, in some embodiments the expression and phosphorylation of one or more polypeptides are detected and quantified using methods of the present invention. As used herein, the term "activation state-specific antibody" or "activation state antibody" or grammatical equivalents thereof, refer to an antibody that specifically binds to a corresponding and specific antigen. Preferably, the corresponding and specific antigen is a specific form of an signaling protein. Also preferably, the binding of the activation state-specific antibody is indicative of a specific activation state of a specific signaling protein.

The term "antibody" includes full length antibodies and antibody fragments, and can refer to a natural antibody from any organism, an engineered antibody, or an antibody generated recombinantly for experimental, therapeutic, or other purposes as further defined below. Examples of antibody fragments, as are known in the art, such as Fab, Fab', F(ab')2, Fv, scFv, or other antigen-binding subsequences of antibodies, either produced by the modification of whole antibodies or those synthesized de novo using recombinant DNA technologies. The term "antibody" comprises monoclonal and polyclonal antibodies. Antibodies can be antagonists, agonists, neutralizing, inhibitory, or stimulatory. They can be humanized, glycosylated, bound to solid supports, and possess other variations.

The antigenicity of an activated isoform of an signaling protein is distinguishable from the antigenicity of non-activated isoform of an signaling protein or from the antigenicity of an isoform of a different activation state. In some embodiments, an activated isoform of an element possesses an epitope that is absent in a non-activated isoform of an element, or vice versa. In some embodiments, this difference is due to covalent addition of moieties to an element, such as phosphate moieties, or due to a structural change in an element, as through protein cleavage, or due to an otherwise induced conformational change in an element which causes the element to present the same sequence in an antigenically distinguishable way. In some embodiments, such a conformational change causes an activated isoform of a signaling protein to present at least one epitope that is not present in a non-activated isoform, or to not present at least one epitope that is presented by a non-activated isoform of the element.

Many antibodies, many of which are commercially available (for example, see Cell Signaling Technology, www.cellsignal.com or Becton Dickinson, www.bd.com) have been produced which specifically bind to the phosphorylated isoform of a protein but do not specifically bind to a non-phosphorylated isoform of a protein. Many such antibodies have been produced for the study of signal transducing proteins which are reversibly phosphorylated. Particularly, many such antibodies have been produced which specifically bind to phosphorylated, activated isoforms of protein. Examples of proteins that can be analyzed with the methods described herein include, but are not limited to, NF-κB, CREB and STAT3.

The methods the invention may utilize affinity reagents comprising a label, labeling element, or tag. By label or labeling element is meant a molecule that can be directly (i.e., a primary label) or indirectly (i.e., a secondary label) detected; for example a label can be visualized and/or measured or otherwise identified so that its presence or absence can be known.

A compound can be directly or indirectly conjugated to a label which provides a detectable signal, e.g. non-radioactive isotopes, radioisotopes, fluorophores, enzymes, antibodies, particles such as magnetic particles, chemiluminescent molecules, molecules that can be detected by mass spec, or specific binding molecules, etc. Specific binding molecules include pairs, such as biotin and streptavidin, digoxin and anti-digoxin etc. Examples of labels include, but are not limited to, metal isotopes, optical fluorescent and chromogenic dyes including labels, label enzymes and radioisotopes. In some embodiments of the invention, these labels can be conjugated to the affinity reagents. In some embodiments, one or more affinity reagents are uniquely labeled.

Labels include optical labels such as fluorescent dyes or moieties. Fluorophores can be either "small molecule" fluors, or proteinaceous fluors (e.g. green fluorescent proteins and all variants thereof). In some embodiments, activation state-specific antibodies are labeled with quantum dots as disclosed by Chattopadhyay et al. (2006) Nat. Med. 12, 972-977. Quantum dot labeled antibodies can be used alone or they can be employed in conjunction with organic fluorochrome—conjugated antibodies to increase the total number of labels available. As the number of labeled antibodies increase so does the ability for subtyping known cell populations.

Activation state-specific antibodies can be labeled using chelated or caged lanthanides as disclosed by Erkki et al. (1988) J. Histochemistry Cytochemistry, 36:1449-1451, and U.S. Pat. No. 7,018,850. Other labels are tags suitable for Inductively Coupled Plasma Mass Spectrometer (ICP-MS) as disclosed in Tanner et al. (2007) Spectrochimica Acta Part B: Atomic Spectroscopy 62(3):188-195. Isotope labels suitable for mass cytometry may be used, for example as described in published application US 2012-0178183.

Alternatively, detection systems based on FRET can be used. FRET find use in the invention, for example, in detecting activation states that involve clustering or multimerization wherein the proximity of two FRET labels is altered due to activation. In some embodiments, at least two fluorescent labels are used which are members of a fluorescence resonance energy transfer (FRET) pair.

When using fluorescent labeled components in the methods and compositions of the present invention, it will recognized that different types of fluorescent monitoring systems, e.g., cytometric measurement device systems, can be used to practice the invention. In some embodiments, flow cytometric systems are used or systems dedicated to high throughput screening, e.g. 96 well or greater microtiter plates. Methods of performing assays on fluorescent materials are well known in the art and are described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N. J., Modern Molecular Photochemistry, Menlo Park: Benjamin/Cummings Publishing Col, Inc. (1978), pp. 296-361.

The detecting, sorting, or isolating step of the methods of the present invention can entail fluorescence-activated cell sorting (FACS) techniques, where FACS is used to select cells from the population containing a particular surface marker, or the selection step can entail the use of magnetically responsive particles as retrievable supports for target cell capture and/or background removal. A variety of FACS systems are known in the art and can be used in the methods of the invention (see e.g., WO99/54494, filed Apr. 16, 1999; U.S. Ser. No. 20010006787, filed Jul. 5, 2001, each expressly incorporated herein by reference).

In some embodiments, a FACS cell sorter (e.g. a FACSVantage™ Cell Sorter, Becton Dickinson Immunocytometry Systems, San Jose, Calif.) is used to sort and collect cells based on their activation profile (positive cells) in the presence or absence of an increase in activation level in an signaling protein in response to a modulator. Other flow cytometers that are commercially available include the LSR II and the Canto II both available from Becton Dickinson. See Shapiro, Howard M., Practical Flow Cytometry, 4th Ed., John Wiley & Sons, Inc., 2003 for additional information on flow cytometers.

In some embodiments, the cells are first contacted with labeled activation state-specific affinity reagents (e.g. antibodies) directed against specific activation state of specific signaling proteins. In such an embodiment, the amount of bound affinity reagent on each cell can be measured by passing droplets containing the cells through the cell sorter. By imparting an electromagnetic charge to droplets containing the positive cells, the cells can be separated from other cells. The positively selected cells can then be harvested in sterile collection vessels. These cell-sorting procedures are described in detail, for example, in the FACSVantage™. Training Manual, with particular reference to sections 3-11 to 3-28 and 10-1 to 10-17, which is hereby incorporated by reference in its entirety. See the patents, applications and articles referred to, and incorporated above for detection systems.

In some embodiments, the activation level of an signaling protein is measured using Inductively Coupled Plasma Mass Spectrometer (ICP-MS). An affinity reagent that has been labeled with a specific element binds to a marker of interest. When the cell is introduced into the ICP, it is atomized and ionized. The elemental composition of the cell, including the labeled affinity reagent that is bound to the signaling protein, is measured. The presence and intensity of the signals corresponding to the labels on the affinity reagent indicates the level of the signaling protein on that cell (Tanner et al. Spectrochimica Acta Part B: Atomic Spectroscopy, 2007 March; 62(3):188-195).

Mass cytometry, e.g. as described in the Examples provided herein, finds use on analysis. Mass cytometry, or CyTOF (DVS Sciences), is a variation of flow cytometry in which antibodies are labeled with heavy metal ion tags rather than fluorochromes. Readout is by time-of-flight mass spectrometry. This allows for the combination of many more antibody specificities in a single samples, without significant spillover between channels. For example, see Bodenmiller at a. (2012) Nature Biotechnology 30:858-867.

STAT signaling pathways. In mammals seven members of the STAT family (STAT1, STAT2, STAT3, STAT4, STAT5a, STAT5b and STAT6) have been identified. JAKs contain two symmetrical kinase-like domains; the C-terminal JAK homology 1 (JH1) domain possesses tyrosine kinase function while the immediately adjacent JH2 domain is enzymatically inert but is believed to regulate the activity of JH1. There are four JAK family members: JAK1, JAK2, JAK3 and tyrosine kinase 2 (Tyk2). Expression is ubiquitous for JAK1, JAK2 and TYK2 but restricted to hematopoietic cells for JAK3.

STATs can be activated in a JAK-independent manner by src family kinase members and by oncogenic FLt3 ligand-ITD (Hayakawa and Naoe, Ann N Y Acad Sci. 2006 November; 1086:213-22; Choudhary et al. Activation mechanisms of STAT5 by oncogenic FLt3 ligand-ITD. Blood (2007) vol. 110 (1) pp. 370-4).

The present invention incorporates information disclosed in other applications and texts. The following patent and other publications are hereby incorporated by reference in their entireties: Alberts et al., The Molecular Biology of the Cell, 4th Ed., Garland Science, 2002; Vogelstein and Kinzler, The Genetic Basis of Human Cancer, 2d Ed., McGraw Hill, 2002; Michael, Biochemical Pathways, John Wiley and Sons, 1999; Weinberg, The Biology of Cancer, 2007; Immunobiology, Janeway et al. 7th Ed., Garland, and Leroith and Bondy, Growth Factors and Cytokines in Health and Disease, A Multi Volume Treatise, Volumes 1A and IB, Growth Factors, 1996.

Unless otherwise apparent from the context, all elements, steps or features of the invention can be used in any combination with other elements, steps or features.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Due to biological functional equivalency considerations, changes can be made in protein structure without affecting the biological action in kind or amount. All such modifications are intended to be included within the scope of the appended claims.

The subject methods are used for prophylactic or therapeutic purposes. As used herein, the term "treating" is used to refer to both prevention of relapses, and treatment of pre-existing conditions. For example, the prevention of inflammatory disease can be accomplished by administration of the agent prior to development of a relapse. The treatment of ongoing disease, where the treatment stabilizes or improves the clinical symptoms of the patient, is of particular interest.

Methods of the Invention

Multiparametric analysis, at a single cell level, of cellular biological samples obtained from an individual during pregnancy is used to obtain a determination of changes in immune cell subsets, which changes include, without limitation, altered activation states of proteins involved in signaling pathways. It is surprisingly found that changes occur in signaling pathways of these immune cells that are predictive of the propensity to develop preeclampsia. For example, multiparameter flow cytometry at the single cell level measures the activation status of multiple intracellular signaling proteins, as well as assigning activation states of these proteins to the varied cell sub-sets within a complex cell population. Flow cytometry includes, without limitations FACS, mass cytometry, and the like.

Protein phosphorylation is a critical post translational process in controlling many cell functions such as migration, apoptosis, proliferation and differentiation. Site specific phosphorylation of proteins can be detected, for example, by incubating cells with labeled phospho-specific antibodies using flow cytometry.

The sample can be any suitable type that allows for the analysis of one or more cells, preferably a blood sample. Samples can be obtained once or multiple times from an individual. Multiple samples can be obtained from different locations in the individual (e.g., blood samples, bone marrow samples and/or lymph node samples), at different times from the individual, or any combination thereof.

When samples are obtained as a series, e.g., a series of blood samples obtained during pregnancy, the samples can be obtained at fixed intervals, at intervals determined by the status of the most recent sample or samples or by other characteristics of the individual, or some combination thereof. It will be appreciated that an interval may not be exact, according to an individual's availability for sampling and the availability of sampling facilities, thus approximate intervals corresponding to an intended interval scheme are encompassed by the invention. Generally, the most easily obtained samples are fluid samples. In some embodiments the sample or samples is blood.

One or more cells or cell types, or samples containing one or more cells or cell types, can be isolated from body samples. The cells can be separated from body samples by red cell lysis, centrifugation, elutriation, density gradient separation, apheresis, affinity selection, panning, FACS, centrifugation with Hypaque, solid supports (magnetic beads, beads in columns, or other surfaces) with attached antibodies, etc. By using antibodies specific for markers identified with particular cell types, a relatively homogeneous population of cells can be obtained. Alternatively, a heterogeneous cell population can be used, e.g. circulating peripheral blood mononuclear cells.

In some embodiments, a phenotypic profile of a population of cells is determined by measuring the activation level of a signaling protein. The methods and compositions of the invention can be employed to examine and profile the status of any signaling protein in a cellular pathway, or collections of such signaling proteins. Single or multiple distinct pathways can be profiled (sequentially or simultaneously), or subsets of signaling proteins within a single pathway or across multiple pathways can be examined (sequentially or simultaneously).

In some embodiments, the basis for classifying cells is that the distribution of activation levels for one or more specific signaling proteins will differ among different phenotypes. A certain activation level, or more typically a range of activation levels for one or more signaling proteins seen in a cell or a population of cells, is indicative that that cell or population of cells belongs to a distinctive phenotype. Other measurements, such as cellular levels (e.g., expression levels) of biomolecules that may not contain signaling proteins, can also be used to classify cells in addition to activation levels of signaling proteins; it will be appreciated that these levels also will follow a distribution. Thus, the activation level or levels of one or more signaling proteins, optionally in conjunction with the level of one or more biomolecules that may or may not contain signaling proteins, of a cell or a population of cells can be used to classify a cell or a population of cells into a class. It is understood that activation levels can exist as a distribution and that an activation level of a particular element used to classify a cell can be a particular point on the distribution but more typically can be a portion of the distribution. In addition to activation levels of intracellular signaling proteins, levels of intracellular or extracellular biomolecules, e.g., proteins, can be used alone or in combination with activation states of signaling proteins to classify cells. Further, additional cellular elements, e.g., biomolecules or molecular complexes such as RNA, DNA, carbohydrates, metabolites, and the like, can be used in conjunction with activation states or expression levels in the classification of cells encompassed here.

In some embodiments of the invention, different gating strategies can be used in order to analyze a specific cell population (e.g., only CD4$^+$ T cells) in a sample of mixed cell population. These gating strategies can be based on the presence of one or more specific surface markers. The following gate can differentiate between dead cells and live cells and the subsequent gating of live cells classifies them into, e.g. myeloid blasts, monocytes and lymphocytes. A clear comparison can be carried out by using two-dimensional contour plot representations, two-dimensional dot plot representations, and/or histograms.

The immune cells are analyzed for the presence of an activated form of a signaling protein of interest. Signaling proteins of interest include, without limitation, pSTAT3, pSTAT1, pCREB, pSTAT6, pPLCγ2, pSTAT5, pSTAT4, pERK, pP38, prpS6, pNF-κB (p65), pMAPKAPK2, and pP90RSK. pSTAT5 is of particular interest. To determine if a change is significant the signal in a patient's baseline sample can be compared to a reference scale from a cohort of patients with known outcomes.

Samples may be obtained at one or more time points. Where a sample at a single time point is used, comparison is made to a reference "base line" level for the presence of the activated form of the signaling protein of interest, which may be obtained from a normal control, a pre-determined level obtained from one or a population of individuals, from a negative control for ex vivo activation, and the like.

When necessary, cells are dispersed into a single cell suspension, e.g. by enzymatic digestion with a suitable protease, e.g. collagenase, dispase, etc; and the like. An appropriate solution is used for dispersion or suspension. Such solution will generally be a balanced salt solution, e.g. normal saline, PBS, Hanks balanced salt solution, etc., conveniently supplemented with fetal calf serum or other naturally occurring factors, in conjunction with an acceptable buffer at low concentration, generally from 5-25 mM. Convenient buffers include HEPES1 phosphate buffers, lactate buffers, etc. The cells can be fixed, e.g. with 3% paraformaldehyde, and are usually permeabilized, e.g. with ice cold methanol; HEPES-buffered PBS containing 0.1% saponin, 3% BSA; covering for 2 min in acetone at −200 C; and the like as known in the art and according to the methods described herein.

In some embodiments, one or more cells are contained in a well of a 96 well plate or other commercially available multiwell plate. In an alternate embodiment, the reaction mixture or cells are in a cytometric measurement device. Other multiwell plates useful in the present invention include, but are not limited to 384 well plates and 1536 well plates. Still other vessels for containing the reaction mixture or cells and useful in the present invention will be apparent to the skilled artisan.

In some embodiment, the methods of the invention include the use of liquid handling components. The liquid handling systems can include robotic systems comprising any number of components. In addition, any or all of the steps outlined herein can be automated; thus, for example, the systems can be completely or partially automated. See U.S. Ser. No. 61/048,657. As will be appreciated by those in the art, there are a wide variety of components which can be used, including, but not limited to, one or more robotic arms; plate handlers for the positioning of microplates; automated lid or cap handlers to remove and replace lids for wells on non-cross contamination plates; tip assemblies for sample distribution with disposable tips; washable tip assemblies for sample distribution; 96 well loading blocks; cooled reagent racks; microtiter plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

In some embodiments, platforms for multi-well plates, multi-tubes, holders, cartridges, minitubes, deep-well plates, microfuge tubes, cryovials, square well plates, filters, chips, optic fibers, beads, and other solid-phase matrices or platform with various volumes are accommodated on an upgradable modular platform for additional capacity. This modular platform includes a variable speed orbital shaker, and multi-position work decks for source samples, sample and reagent dilution, assay plates, sample and reagent reservoirs, pipette tips, and an active wash station. In some embodiments, the methods of the invention include the use of a plate reader.

In some embodiments, interchangeable pipet heads (single or multi-channel) with single or multiple magnetic probes, affinity probes, or pipetters robotically manipulate the liquid, particles, cells, and organisms. Multi-well or multi-tube magnetic separators or platforms manipulate liquid, particles, cells, and organisms in single or multiple sample formats.

In some embodiments, the instrumentation will include a detector, which can be a wide variety of different detectors, depending on the labels and assay. In some embodiments, useful detectors include a microscope(s) with multiple channels of fluorescence; plate readers to provide fluorescent, ultraviolet and visible spectrophotometric detection with single and dual wavelength endpoint and kinetics capability, fluorescence resonance energy transfer (FRET), luminescence, quenching, two-photon excitation, and intensity redistribution; CCD cameras to capture and transform data and images into quantifiable formats; and a computer workstation.

In some embodiments, the robotic apparatus includes a central processing unit which communicates with a memory and a set of input/output devices (e.g., keyboard, mouse, monitor, printer, etc.) through a bus. Again, as outlined below, this can be in addition to or in place of the CPU for the multiplexing devices of the invention. The general interaction between a central processing unit, a memory, input/output devices, and a bus is known in the art. Thus, a variety of different procedures, depending on the experiments to be run, are stored in the CPU memory.

The differential presence of these markers is shown to provide for prognostic evaluations to detect individuals having a propensity to develop preeclampsia. In general, such prognostic methods involve determining the presence or level of activated signaling proteins in an individual sample of immune cells. Detection can utilize one or a panel of specific binding members, e.g. a panel or cocktail of binding members specific for one, two, three, four, five or more markers.

Data Analysis

A signature pattern can be generated from a biological sample using any convenient protocol, for example as described below. The readout can be a mean, average, median or the variance or other statistically or mathematically-derived value associated with the measurement. The marker readout information can be further refined by direct comparison with the corresponding reference or control pattern. A binding pattern can be evaluated on a number of points: to determine if there is a statistically significant change at any point in the data matrix relative to a reference value; whether the change is an increase or decrease in the binding; whether the change is specific for one or more physiological states, and the like. The absolute values obtained for each marker under identical conditions will display a variability that is inherent in live biological systems and also reflects the variability inherent between individuals.

Following obtainment of the signature pattern from the sample being assayed, the signature pattern can be compared with a reference or base line profile to make a prognosis regarding the phenotype of the patient from which the sample was obtained/derived. Additionally, a reference or control signature pattern can be a signature pattern that is obtained from a sample of a patient known to have a normal pregnancy.

In certain embodiments, the obtained signature pattern is compared to a single reference/control profile to obtain information regarding the phenotype of the patient being assayed. In yet other embodiments, the obtained signature pattern is compared to two or more different reference/control profiles to obtain more in depth information regarding the phenotype of the patient. For example, the obtained signature pattern can be compared to a positive and negative reference profile to obtain confirmed information regarding whether the patient has the phenotype of interest.

Samples can be obtained from the tissues or fluids of an individual. For example, samples can be obtained from whole blood, tissue biopsy, serum, etc. Other sources of samples are body fluids such as lymph, cerebrospinal fluid, and the like. Also included in the term are derivatives and fractions of such cells and fluids In order to identify profiles that are indicative of responsiveness, a statistical test can provide a confidence level for a change in the level of markers between the test and reference profiles to be considered significant. The raw data can be initially analyzed by measuring the values for each marker, usually in duplicate, triplicate, quadruplicate or in 5-10 replicate features per marker. A test dataset is considered to be different than a reference dataset if one or more of the parameter values of the profile exceeds the limits that correspond to a predefined level of significance.

To provide significance ordering, the false discovery rate (FDR) can be determined. First, a set of null distributions of dissimilarity values is generated. In one embodiment, the values of observed profiles are permuted to create a sequence of distributions of correlation coefficients obtained out of chance, thereby creating an appropriate set of null distributions of correlation coefficients (see Tusher et al. (2001) PNAS 98, 5116-21, herein incorporated by reference). This analysis algorithm is currently available as a software "plug-in" for Microsoft Excel know as Significance Analysis of Microarrays (SAM). The set of null distribution is obtained by: permuting the values of each profile for all available profiles; calculating the pair-wise correlation coefficients for all profile; calculating the probability density function of the correlation coefficients for this permutation; and repeating the procedure for N times, where N is a large number, usually 300. Using the N distributions, one calculates an appropriate measure (mean, median, etc.) of the count of correlation coefficient values that their values exceed the value (of similarity) that is obtained from the distribution of experimentally observed similarity values at given significance level.

The FDR is the ratio of the number of the expected falsely significant correlations (estimated from the correlations greater than this selected Pearson correlation in the set of randomized data) to the number of correlations greater than this selected Pearson correlation in the empirical data (significant correlations). This cut-off correlation value can be applied to the correlations between experimental profiles.

For SAM, Z-scores represent another measure of variance in a dataset, and are equal to a value of X minus the mean of X, divided by the standard deviation. A Z-Score tells how a single data point compares to the normal data distribution. A Z-score demonstrates not only whether a datapoint lies above or below average, but how unusual the measurement is. The standard deviation is the average distance between each value in the dataset and the mean of the values in the dataset.

Using the aforementioned distribution, a level of confidence is chosen for significance. This is used to determine the lowest value of the correlation coefficient that exceeds the result that would have obtained by chance. Using this method, one obtains thresholds for positive correlation, negative correlation or both. Using this threshold(s), the user can filter the observed values of the pairwise correlation coefficients and eliminate those that do not exceed the threshold(s). Furthermore, an estimate of the false positive rate can be obtained for a given threshold. For each of the individual "random correlation" distributions, one can find how many observations fall outside the threshold range. This procedure provides a sequence of counts. The mean and the standard deviation of the sequence provide the average number of potential false positives and its standard deviation. Alternatively, any convenient method of statistical validation can be used.

The data can be subjected to non-supervised hierarchical clustering to reveal relationships among profiles. For example, hierarchical clustering can be performed, where the Pearson correlation is employed as the clustering metric. One approach is to consider a patient disease dataset as a "learning sample" in a problem of "supervised learning". CART is a standard in applications to medicine (Singer (1999) Recursive Partitioning in the Health Sciences, Springer), which can be modified by transforming any qualitative features to quantitative features; sorting them by attained significance levels, evaluated by sample reuse methods for Hotellling's $T^2$ statistic; and suitable application of the lasso method. Problems in prediction are turned into problems in regression without losing sight of prediction, indeed by making suitable use of the Gini criterion for classification in evaluating the quality of regressions.

Other methods of analysis that can be used include logistic regression. One method of logic regression Ruczinski (2003) Journal of Computational and Graphical Statistics 12:475-512. Logic regression resembles CART in that its classifier can be displayed as a binary tree. It is different in that each node has Boolean statements about features that are more general than the simple "and" statements produced by CART.

Another approach is that of nearest shrunken centroids (Tibshirani (2002) PNAS 99:6567-72). The technology is k-means-like, but has the advantage that by shrinking cluster centers, one automatically selects features (as in the lasso) so as to focus attention on small numbers of those that are informative. The approach is available as Prediction Analysis of Microarrays (PAM) software, a software "plug-in" for Microsoft Excel, and is widely used. Two further sets of algorithms are random forests (Breiman (2001) Machine Learning 45:5-32 and MART (Hastie (2001) The Elements of Statistical Learning, Springer). These two methods are already "committee methods." Thus, they involve predictors that "vote" on outcome. Several of these methods are based on the "R" software, developed at Stanford University, which provides a statistical framework that is continuously being improved and updated in an ongoing basis.

Other statistical analysis approaches including principle components analysis, recursive partitioning, predictive algorithms, Bayesian networks, and neural networks.

These tools and methods can be applied to several classification problems. For example, methods can be developed from the following comparisons: i) all cases versus all controls, ii) all cases versus nonresponsive controls, iii) all cases versus responsive controls.

In a second analytical approach, variables chosen in the cross-sectional analysis are separately employed as predictors. Given the specific outcome, the random lengths of time each patient will be observed, and selection of proteomic and other features, a parametric approach to analyzing responsiveness can be better than the widely applied semi-parametric Cox model. A Weibull parametric fit of survival permits the hazard rate to be monotonically increasing, decreasing, or constant, and also has a proportional hazards representation (as does the Cox model) and an accelerated failure-time representation. All the standard tools available in obtaining approximate maximum likelihood estimators of regression coefficients and functions of them are available with this model.

In addition the Cox models can be used, especially since reductions of numbers of covariates to manageable size with the lasso will significantly simplify the analysis, allowing the possibility of an entirely nonparametric approach to survival.

The analysis and database storage can be implemented in hardware or software, or a combination of both. In one embodiment of the invention, a machine-readable storage medium is provided, the medium comprising a data storage material encoded with machine readable data which, when using a machine programmed with instructions for using said data, is capable of displaying a any of the datasets and data comparisons of this invention. Such data can be used for a variety of purposes, such as patient monitoring, initial diagnosis, and the like. Preferably, the invention is implemented in computer programs executing on programmable computers, comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer can be, for example, a personal computer, microcomputer, or workstation of conventional design.

Each program is preferably implemented in a high level procedural or object oriented programming language to communicate with a computer system. However, the programs can be implemented in assembly or machine language, if desired. In any case, the language can be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system can also be considered to be implemented as a computer-readable storage medium, configured with a computer program, where the storage medium so configured causes a computer to operate in a specific and predefined manner to perform the functions described herein.

A variety of structural formats for the input and output means can be used to input and output the information in the computer-based systems of the present invention. One format for an output means test datasets possessing varying degrees of similarity to a trusted profile. Such presentation provides a skilled artisan with a ranking of similarities and identifies the degree of similarity contained in the test pattern.

The signature patterns and databases thereof can be provided in a variety of media to facilitate their use. "Media" refers to a manufacture that contains the signature pattern information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure can be chosen, based on the means used to access the stored information. A variety of data processor programs and formats can be used for storage, e.g. word processing text file, database format, etc.

Kits

In some embodiments, the invention provides kits for the classification, diagnosis, prognosis, theranosis, and/or prediction of an outcome during pregnancy in a subject. The kit may further comprise a software package for data analysis of the cellular state and its physiological status, which may include reference profiles for comparison with the test profile and comparisons to other analyses as referred to above. The kit may also include instructions for use for any of the above applications.

Kits provided by the invention may comprise one or more of the affinity reagents described herein, such as phospho-specific antibodies and antibodies that distinguish subsets of immune cells. A kit may also include other reagents that are useful in the invention, such as modulators, fixatives, containers, plates, buffers, therapeutic agents, instructions, and the like.

Kits provided by the invention can comprise one or more labeling elements. Non-limiting examples of labeling elements include small molecule fluorophores, proteinaceous fluorophores, radioisotopes, enzymes, antibodies, chemiluminescent molecules, biotin, streptavidin, digoxigenin, chromogenic dyes, luminescent dyes, phosphorous dyes, luciferase, magnetic particles, beta-galactosidase, amino groups, carboxy groups, maleimide groups, oxo groups and thiol groups, quantum dots, chelated or caged lanthanides, isotope tags, radiodense tags, electron-dense tags, radioactive isotopes, paramagnetic particles, agarose particles, mass tags, e-tags, nanoparticles, and vesicle tags.

In some embodiments, the kits of the invention enable the detection of signaling proteins by sensitive cellular assay methods, such as IHC and flow cytometry, which are suitable for the clinical detection, classification, diagnosis, prognosis, theranosis, and outcome prediction.

Such kits may additionally comprise one or more therapeutic agents. The kit may further comprise a software package for data analysis of the physiological status, which may include reference profiles for comparison with the test profile.

Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

Reports

In some embodiments, providing an evaluation of a subject for a classification, diagnosis, prognosis, theranosis, and/or prediction of an outcome during pregnancy includes generating a written report that includes the artisan's assessment of the subject's state of health i.e. a "diagnosis assessment", of the subject's prognosis, i.e. a "prognosis assessment", and/or of possible treatment regimens, i.e. a "treatment assessment". Thus, a subject method may further include a step of generating or outputting a report providing the results of a diagnosis assessment, a prognosis assessment, or treatment assessment, which report can be provided in the form of an electronic medium (e.g., an electronic display on a computer monitor), or in the form of a tangible medium (e.g., a report printed on paper or other tangible medium).

A "report," as described herein, is an electronic or tangible document which includes report elements that provide information of interest relating to a diagnosis assessment, a prognosis assessment, and/or a treatment assessment and its results. A subject report can be completely or partially electronically generated. A subject report includes at least a diagnosis assessment, i.e. a diagnosis as to whether a subject will have a particular clinical responseduring pregnancy, and/or a suggested course of treatment to be followed. A subject report can further include one or more of: 1) information regarding the testing facility; 2) service provider information; 3) subject data; 4) sample data; 5) an assessment report, which can include various information including: a) test data, where test data can include an analysis of cellular signaling responses to activation, b) reference values employed, if any.

The report may include information about the testing facility, which information is relevant to the hospital, clinic, or laboratory in which sample gathering and/or data generation was conducted. This information can include one or more details relating to, for example, the name and location of the testing facility, the identity of the lab technician who conducted the assay and/or who entered the input data, the date and time the assay was conducted and/or analyzed, the location where the sample and/or result data is stored, the lot number of the reagents (e.g., kit, etc.) used in the assay, and the like. Report fields with this information can generally be populated using information provided by the user.

The report may include information about the service provider, which may be located outside the healthcare facility at which the user is located, or within the healthcare facility. Examples of such information can include the name and location of the service provider, the name of the reviewer, and where necessary or desired the name of the individual who conducted sample gathering and/or data generation. Report fields with this information can generally be populated using data entered by the user, which can be selected from among pre-scripted selections (e.g., using a drop-down menu). Other service provider information in the report can include contact information for technical information about the result and/or about the interpretive report.

The report may include a subject data section, including subject medical history as well as administrative subject data (that is, data that are not essential to the diagnosis, prognosis, or treatment assessment) such as information to identify the subject (e.g., name, subject date of birth (DOB), gender, mailing and/or residence address, medical record number (MRN), room and/or bed number in a healthcare facility), insurance information, and the like), the name of the subject's physician or other health professional who ordered the susceptibility prediction and, if different from the ordering physician, the name of a staff physician who is responsible for the subject's care (e.g., primary care physician).

The report may include a sample data section, which may provide information about the biological sample analyzed, such as the source of biological sample obtained from the subject (e.g. blood, type of tissue, etc.), how the sample was handled (e.g. storage temperature, preparatory protocols) and the date and time collected. Report fields with this information can generally be populated using data entered by the user, some of which may be provided as pre-scripted selections (e.g., using a drop-down menu).

The report may include an assessment report section, which may include information generated after processing of the data as described herein. The interpretive report can include a prognosis of the likelihood that the patient will develop preeclampsia. The interpretive report can include, for example, results of the analysis, methods used to calculate the analysis, and interpretation, i.e. prognosis. The assessment portion of the report can optionally also include a Recommendation(s). For example, where the results indicate the subject's prognosis for propensity to develop preeclampsia.

It will also be readily appreciated that the reports can include additional elements or modified elements. For example, where electronic, the report can contain hyperlinks which point to internal or external databases which provide more detailed information about selected elements of the report. For example, the patient data element of the report can include a hyperlink to an electronic patient record, or a site for accessing such a patient record, which patient record is maintained in a confidential database. This latter embodiment may be of interest in an in-hospital system or in-clinic setting. When in electronic format, the report is recorded on a suitable physical medium, such as a computer readable medium, e.g., in a computer memory, zip drive, CD, DVD, etc.

It will be readily appreciated that the report can include all or some of the elements above, with the proviso that the report generally includes at least the elements sufficient to provide the analysis requested by the user (e.g., a diagnosis, a prognosis, or a prediction of responsiveness to a therapy).

Therapeutic Intervention

Low dose IL-2 promotes selective expansion of regulatory T cells (Treg), and can be beneficial in normalizing the immune state of patients determined to be at risk of developing preeclampsia. The IL-2 administered according to the methods described herein may come from any appropriate source. The term "IL-2" designates any source of IL-2, including mammalian sources such as e.g., human, mouse, rat, primate, and pig, and may be native or obtained by recombinant or synthetic techniques, including recombinant IL-2 polypeptides produced by microbial hosts. IL-2 may be or comprise the native polypeptide sequence or can be an active variant of the native IL-2 polypeptide. Preferably the IL-2 polypeptide or active variant is derived from a human source, and includes recombinant human IL-2, particularly recombinant human IL-2 produced by microbial hosts.

Active variants of IL-2 have been disclosed in the literature. Variants of the native IL-2 can be fragments, analogues, and derivatives thereof. By "fragment" is intended a polypeptide comprising only a part of the intact polypeptide sequence. An "analogue" designates a polypeptide comprising the native polypeptide sequence with one or more amino acid substitutions, insertions, or deletions. Muteins and pseudopeptides are specific examples of analogues, IL-2 N88R is a specific mutein with diminished binding to the intermediate affinity IL-2R βγ. "Derivatives" include any modified native IL-2 polypeptide or fragment or analogue thereof, such as glycosylated, phosphorylated, fused to another polypeptide or molecule, polymerized, etc., or through chemical or enzymatic modification or addition to improve the properties of IL-2 (e.g., stability, specificity, etc.). Active variants of a reference IL-2 polypeptide generally have at least 75%, preferably at least 85%, more preferably at least 90% amino acid sequence identity to the amino acid sequence of the reference IL-2 polypeptide.

Methods for determining whether a variant IL-2 polypeptide is active are available in the art and are specifically described in the present invention. An active variant is, most preferably, a variant that activates Tregs. Examples of IL-2 variants are disclosed, for instance, in EP109748, EP136489, U.S. Pat. No. 4,752,585; EP200280, or EP118,617.

Preferably a recombinant IL-2 is used i.e., an IL-2 that has been prepared by recombinant DNA techniques. In a preferred embodiment, the invention uses an IL-2 of human origin, or an active variant thereof, more preferably produced recombinantly. A nucleotide and an amino acid sequence of human IL-2 are disclosed, for instance, in Genbank ref 3558 or P60568, respectively. The invention more preferably uses a human IL-2. IL-2 for use in the present invention may be in essentially pure form, e.g., at a purity of 95% or more, further preferably 96, 97, 98 or 99% pure.

IL-2 is commercially available, including for pharmaceutical uses, and it is authorized for use in human patients. Suitable commercial forms include, e.g., Proleukin™, a recombinant, human IL-2 composition, Aldesleukin™, an unglycosylated des-alanyl-1, serine-125 human interleukin-2 produced in *E. coli*. Roncoleukin™, recombinant human IL-2 produced in yeast.

Provided herein is a method of administering interleukin-2 at a low dose sufficient to expand regulatory T lymphocytes (Tregs) without substantially inducing effector T lymphocytes (Teffs), as distinct from a high dose that is sufficient to expand Teffs. A low dose of IL-2 is generally at least about 10-fold lower than a conventional high dose, (where a high dose may be, for example, from about 700 IU/kg/day, or from about $50 \times 10^6$ to $150 \times 10^6$ IU/day for an average human body weight). Dosage ranges described herein are provided as the dose that is administered in a one day period of time, in terms of the body surface area ($m^2$), and international units (IU). A daily dose may be fractionated into 1, 2, 3, or 4 separate doses over a day.

A low dose of IL-2 is administered at a dose of about $0.05 \times 10^6$ to not more than about $5 \times 10^6$ international unit (IU)/$m^2$/day, not more than about $4 \times 10^6$ IU/$m^2$/day, not more than about $3 \times 10^6$ IU/$m^2$/day, not more than about $2 \times 10^6$ IU/$m^2$/day, not more than about $1 \times 10^6$ IU/$m^2$/day. Preferably the dose is at least about $0.1 \times 10^6$ IU/$m^2$/day, at least about $0.2 \times 10^6$ IU/$m^2$/day, at least about $0.3 \times 10^6$ IU/$m^2$/day; and may be from about $0.4 \times 10^6$ IU/$m^2$/day, $0.5 \times 10^6$ IU/$m^2$/day, $0.6 \times 10^6$ IU/$m^2$/day, $0.7 \times 10^6$ IU/$m^2$/day, $0.8 \times 10^6$ IU/$m^2$/day, $0.9 \times 10^6$ IU/$m^2$/day, $1 \times 10^6$ IU/$m^2$/day, $2 \times 10^6$ IU/$m^2$/day.

The treatment may comprise a course wherein interleukin-2 is administered in a dose once per day (or fractionated into multiple doses over the day), and may be administered for at least 3 consecutive days, for 3 to 7 consecutive days, for 4 to 5 consecutive days, etc. Treatment may be maintained for extended period of time, e.g. over one month, 2 months, up to the completion of the third trimester of pregnancy. The dose can be administered daily, every 2 days, every 3 days, twice per week, once per week, every 2 weeks, or once or more a month. In some embodiments, the IL-2 is administered once per day, once every 2 days, once every 3 days, twice per week, once per week, once every 2 weeks, or once or more a month.

In one embodiment, the treatment comprises a course wherein an initial dose in a range disclosed above is administered once or twice a day during at least 3 consecutive days, preferably during 3 to 7 consecutive days, still preferably 4 to 5 consecutive days, followed by a maintenance dose after one to three weeks, which maintenance dose can be repeated every one to three weeks.

IL-2 for the purposes of the present invention is usually administered at a dose triggering up-regulation of expression of CD25 in Treg. Preferably the up-regulation of expression of CD25 is at least 33%, preferably at least 50%, where up-regulation of CD25 can be determined by, for example, antibody staining and flow cytometry analysis of peripheral blood T cells for expression of CD25, e.g. by analysis of $CD4^+$ cells in peripheral blood for upregulation of CD25.

As used herein, a stimulation (or induction or activation or amplification) of Treg designates any increase in proportion of Treg cells relative to Teffs, in number or in activity as tested by suppressive assays or by expression of molecules that reflect the activity of the Tregs such as pSTAT5, CD25, the alpha-chain of the IL-2 receptor, Foxp3, or GITR in a patient. The augmentation in proportion is preferably by at least about 20% as compared to the level prior to treatment, more preferably at least about 40%, even more preferably at least about 60%.

One biomarker for efficacy of low dose IL-2 is an increase in the ratio of Tregs to Teffs. In a particular and preferred embodiment, an effective treatment provides for a shift in the Treg/Teff balance towards Tregs, or an increase in the Treg/Teff ratio or an increase in the inherent regulatory capacity of Tregs from the treated subject. The total number of Treg cells as a percent of total CD4+ cells in peripheral blood may initially range from around about 1%, around about 2%, around about 3%, around about 4% around about 5% up to about 10%, about 15%, about 20% or more. The augmentation in proportion is preferably by at least about 20% as compared to the level prior to treatment, more preferably at least about 40%, even more preferably at least about 60%.

The stimulation of Treg and absence of substantial induction of Teff is preferably assessed by a measure of the ratio or the balance Treg/Teff in the treated subject. This balance is calculated e.g., based on the number of Tregs and the number of Teff in a sample from the subject. Such a balance typically increases by at least about 20% in the treated patients, more preferably by at least about 30%, at least about 40%, at least about 60%, or more relative to an untreated control.

Effective expansion of Tregs may be measured by an increase in absolute numbers of Treg cells in the patient, typically by at least about 10%, at least about 20%, at least 30% or more in number relative to the starting population. Expansion may be measured by an increase in activation markers on Treg cells, such as the intensity of CD25 or FoxP3 expression or pSTAT5, e.g. at least about 10%, at least about 20%, at least about 30% or more increase relative to an untreated control.

Alternatively an increase in Treg activity may be determined in an in vitro assay by the number of Tregs from a treated patient required to give 50% reduction in response to activating the Teffs from the same patient. In a normal patient the ratio is from about 1:2, from about 1:4, to about 1:10 Tregs to Teffs, and an increase may be by at least about 20% in the treated patients, more preferably by at least about 30%, at least about 40%, at least about 60%, or more relative to an untreated control.

The absence of substantial induction (or activation or expansion) of Teff can also be measured by measuring the number of Teff and/or the activity of Teff in samples from the treated subject. The absence of substantial induction indicates the target Teff cell population does not acquire markers of activation such as CD25, CD69, and/or HLA-DR, or as assessed by whole transcriptome analyses. An absence of Teff induction typically designates that the Teff cell population has not increased by more than 10% in said subject as a result of treatment. Detailed methods for detecting, measuring and quantifying Treg and Teff cells are known in the art.

IL-2 may be administered using any acceptable method known per se in the art. Thus, for example, IL-2, or the pharmaceutical composition comprising IL-2, can be administered by any form of injection, including intravenous (IV), intramuscular (IM), or transdermal or subcutaneous (SC) injection, or by oral or nasal route as well as by topical administration (cream, droplets, etc.). or in slow release formulation. IL-2 can be used as a sustained-release formulation, or a formulation that is administered using a sustained release device. Such devices are well known in the art, and include, for example, transdermal patches, and miniature implantable pumps that can provide for drug delivery over time in a continuous, steady-state fashion at a variety of doses to achieve a sustained-release effect. Sublingual or eye drop formulations may also be contemplated.

EXPERIMENTAL

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Differential Dynamics of the Maternal Immune System in Healthy Pregnancy and Preeclampsia A healthy pregnancy relies on a dynamic immunological interplay between the mother and fetus. Severe pregnancy complications may arise when this interplay is disrupted. We performed an in-depth analysis comparing maternal immune system dynamics in healthy pregnancies and in preeclampsia, one of the most severe pregnancy complications and a leading cause of maternal death. We used a high-dimensional mass cytometry immunoassay to characterize the dynamic changes of over 480 immune cell features (including cell distribution and functional responses) in maternal blood during healthy and preeclamptic pregnancies. We found a set of eight cell-specific immune features that accurately identified patients well before the clinical diagnosis of preeclampsia (median area under the curve (AUC) 0.91, interquartile range [0.82-0.92]). Several features recapitulated previously known immune dysfunctions in preeclampsia, such as elevated pro-inflammatory innate immune responses early in pregnancy and impaired regulatory T (Treg) cell signaling. The analysis revealed additional novel immune responses that were strongly associated with, and preceded the onset of preeclampsia, notably abnormal STAT5ab signaling dynamics in $CD4^+T$ cell subsets (AUC 0.92, p=8.0E-5). These results provide a global readout of the dynamics of the maternal immune system early in pregnancy and lay the groundwork for identifying clinically-relevant immune dysfunctions for the prediction and prevention of preeclampsia.

Systemic inflammation and alterations in the normal immune adaptations necessary for the maintenance of a healthy pregnancy are central features in the pathophysiology of preeclampsia. Accumulating evidence suggests that preeclampsia is associated with a breakdown of tolerogenic cellular adaptations, including a shift in T cell distributions towards Th1 and Th17 and away from Th2 and regulatory $CD4^+T$ cell (Treg) populations. The potential role of the maternal immune system in the pathogenesis of preeclampsia was underscored by a recent multi-omic study of placental, coagulation, complement and vascular factors, highlighting that a majority of plasma proteins associated with preeclampsia were linked to immune functions.

Immune dysfunction may be detected well before the clinical onset of preeclampsia, as early as during the first trimester of pregnancy. For this reason, identifying immunological attributes in maternal blood that predict and help prevent preeclampsia at a preclinical state is of considerable clinical interest. However, due to limitations in assay technology, prior studies of immune responses associated with preeclampsia have been restricted to a select number of cell subsets and may not have captured immune cell behaviors in the context of the entire peripheral immune system. In particular, the limited number of parameters available for the phenotypic and functional characterization of immune cell subsets may have hampered the detection of important cellular and functional signatures.

Recently developed, highly multiplex single-cell technologies such as mass cytometry—a flow cytometry platform that allows assessment of over 40 parameters on a cell-by-cell basis—offer unprecedented opportunities for comprehensive functional studies of the human immune system. Combined with appropriate statistical tools that account for the high-dimensionality of the data, mass cytometry is uniquely capable of identifying alterations of the human immune system associated with normal physiological perturbations and disease pathogenesis.

In a recent study, we employed a high-parameter mass cytometry assay to characterize the dynamic changes in maternal immune cell distribution and signaling responses during an uncomplicated pregnancy. Here, we report on an in-depth profiling of the dynamics of the maternal immune system in healthy (normotensive) pregnancies and preeclampsia. Our primary goal was to detect characteristic immune dysfunctions in the maternal blood prior to the clinical onset of preeclampsia.

Results

Study cohort. The 11 study participants with preeclampsia were slightly younger and heavier than the 12 study participants from the control group (Table 1). Seven of the women with preeclampsia had severe features, and two had early-onset preeclampsia (including one patient with severe features). Participants with preeclampsia had more comorbidities, including arterial hypertension, diabetes, and autoimmune diseases, including lupus erythematosus (Table 1). Samples were collected well before clinical diagnosis of preeclampsia: a median of 13 weeks (interquartile range (IQR), 12 to 14). The gestational age (GA) at time of sampling did not differ between the two groups (median at the first time point (T1): 11 vs. 11 weeks, p=0.48; median at the second time point (T2): 25.5 vs. 25 weeks, p=0.36).

Figure 6:
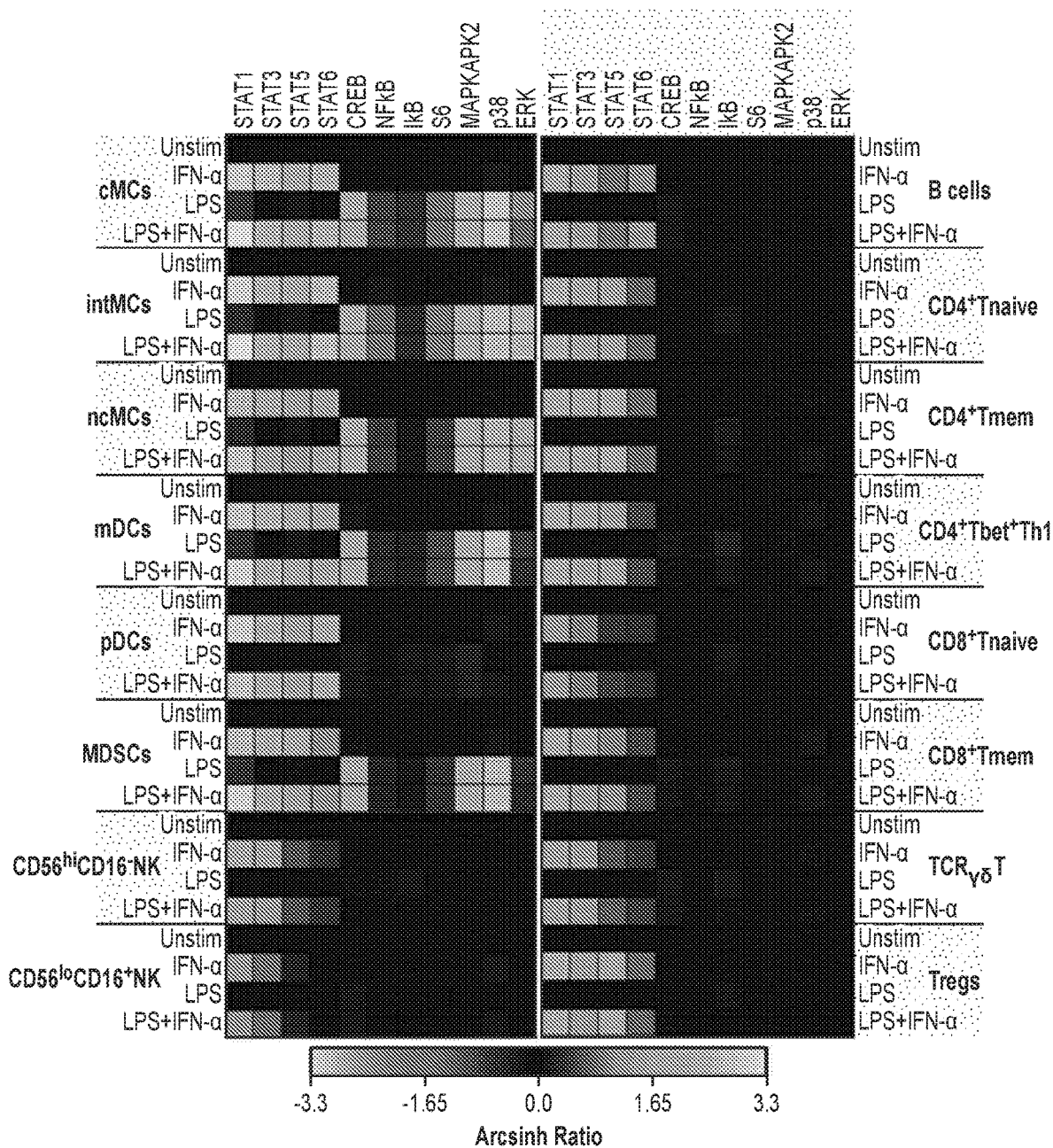
FIG. 6. Optimization of the stimulation condition. PBMC sample availability allowed for only one stimulation to be performed. LPS and IFN-α were utilized in combination to maximize the functional information obtained from the stimulated samples. Blood samples from a healthy volunteer was left unstimulated (first row) or stimulated with LPS alone (1 µg/mL, second row), IFN-α alone (100 ng/mL, third row), or both (fourth row) for 15 min and analyzed using mass cytometry. The heatmaps show that the mass cytometry immunoassay detected little overlap in immune cell signaling activities in response to LPS and IFN-α alone. Immune signaling responses to LPS were restricted to pERK1/2, pP38, pMAPKAPK2, pS6, pCREB, pNF-κB and total IκB in innate immune cells. Immune signaling response to IFN-α were restricted to pSTAT1, pSTAT3. pSTAT5, pSTAT6 in innate and adaptive immune cells).
Figure 8A:
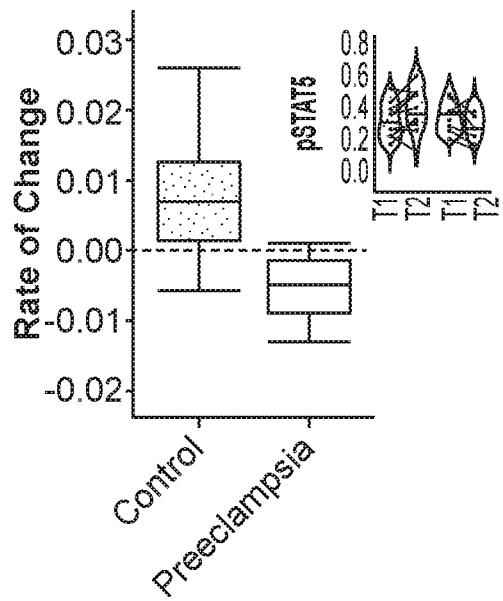
FIG. 8A-8D. pSTAT5 signal (basal) in CD4$^+$T subsets. Total CD4$^+$T cells (FIG. 8A), CD4$^+$T naive (FIG. 8B), CD4$^+$Tmem (FIG. 8C), CD25$^+$FoxP3$^+$Tregs (FIG. 8D). Boxplots (left panel) depict immune feature rate of change for controls (purple) and preeclampsia (orange) study participants. Insets (right panels): Immune feature values (arcsinh transform of mass cytometry intracellular signal mean intensity) are represented for individual time points and for each patient (lines).
Figure 8B:
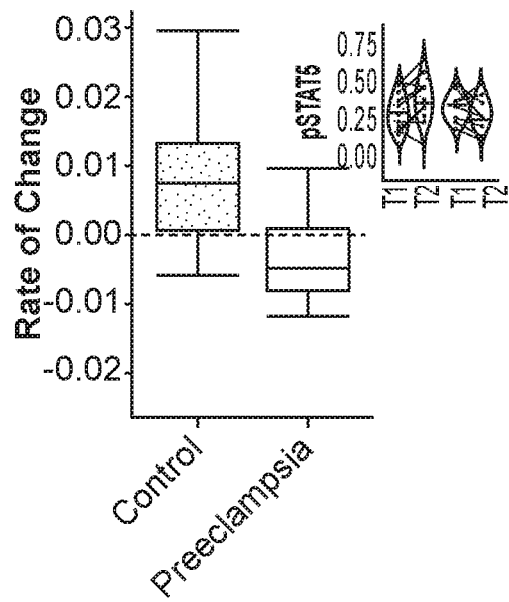
Figure 8C:
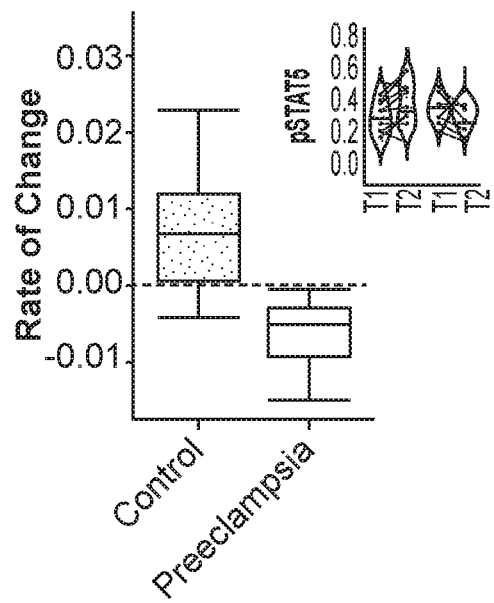
Figure 8D:
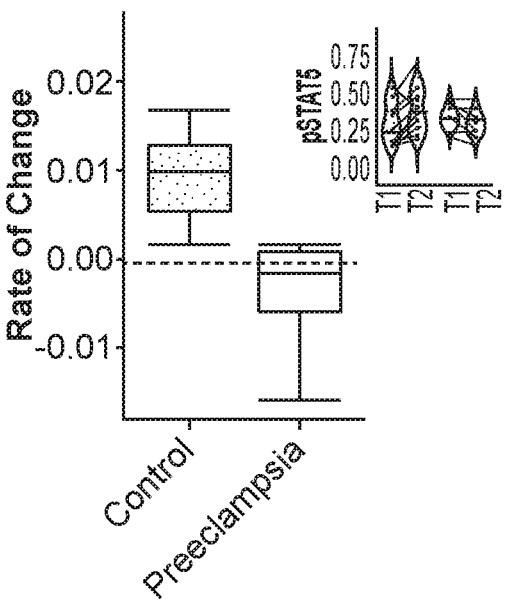

Deep profiling of maternal immune responses in healthy and preeclamptic pregnancies. Peripheral blood mononuclear cells (PBMCs) collected longitudinally during pregnancy were analyzed using a 41-parameter immunoassay for an in-depth profiling of peripheral immune cell adaptations. For each patient sample, 483 immune features were quantified on a per cell basis in 21 distinct innate and adaptive immune cell subsets (FIG. 1). Immune features included cell frequencies and the activity (e.g. phosphorylation state) of 11 intracellular signaling proteins measured at baseline (basal signaling activity) as well as in response to extracellular stimulations with interferon-α (IFN-α) and lipopolysaccharide (LPS) (FIG. 1, FIG. 6). Stimulation conditions were chosen to activate receptor-specific signaling responses (Toll-Like Receptor (TLR) 4-dependent signaling for LPS, Janus kinase (JAK)-Signal Transducer and Activator of Transcription (STAT) signaling for IFN-α) that were most informative in characterizing immune cell dynamics in our previous mass cytometry analyses of healthy pregnancies.

The high-parameter immunological dataset yielded a correlation network that emphasized the interconnectivity of immune responses during pregnancy (FIG. 1). The correlation network segregated into 14 communities of closely interconnected immune features. Communities were identified based on the immune feature characteristic (cell types and/or intracellular functional response) that appeared most frequently (FIG. 2A). In the control group, a targeted examination of select communities revealed peripheral immune cell adaptations that dovetailed with prior immune profiling studies of normal pregnancy. For instance, one of the communities (Community 2) was defined by the basal activity of the transcription factor STAT5ab (phospho, pSTAT5 signal) in $CD4^+T$ cells (FIG. 7A), which increased during pregnancy. Another community (Community 7) contained features that pointed at increasing pSTAT1 responses to stimulation in NK cells during pregnancy (FIG. 7B), consistent with in vitro and in vivo studies showing that NK cell-mediated pathogen responses are exacerbated during pregnancy. In addition, Treg cell frequency increased between the first and second trimesters of pregnancy (FIG. 7C), consistent with reports of Treg dynamics during pregnancy. Thus, the immunoassay utilized in this study was sensitive to detect established hallmarks of maternal immune adaptations during a normal pregnancy.

Immune system-wide dynamics are disrupted in preeclampsia. A number of observations in humans support the assessment of immune cell responses over time, rather than a cross-sectional assessment at a given time point, to understand how the human immune system adapts to a physiological or a pathological perturbation. We reasoned that an analysis focused on immune response dynamics would be particularly adapted to detect immune dysfunctions preceding the onset of preeclampsia.

To parameterize the dynamic changes in the peripheral immune system during pregnancy, the rate of change between the first and second sampling time points was calculated for each immune feature. The least absolute shrinkage and selection operator (LASSO) method was applied to the dataset of immune feature dynamics. The predictive analysis identified a multivariate model that accurately differentiated women who developed preeclampsia from controls (FIG. 2B-C). Components of the LASSO model were visualized on the correlation network as red or blue nodes highlighting immune features with accelerated or decelerated, respectively, dynamics in women who will develop preeclampsia (FIG. 2B). The generalizability of the model was established using a stringent cross-validation method that accounts for the high-dimensionality of the dataset. No significant association was found between the LASSO model prediction and the presence of comorbid conditions, including autoimmune diseases, gestational diabetes, chronic hypertension and body mass index (BMI). The results suggest that specific aspects of peripheral immune system dynamics, detectable 12 to 14 weeks before the clinical diagnosis of preeclampsia, are disrupted in preeclamptic pregnancies.

Figure 3A:
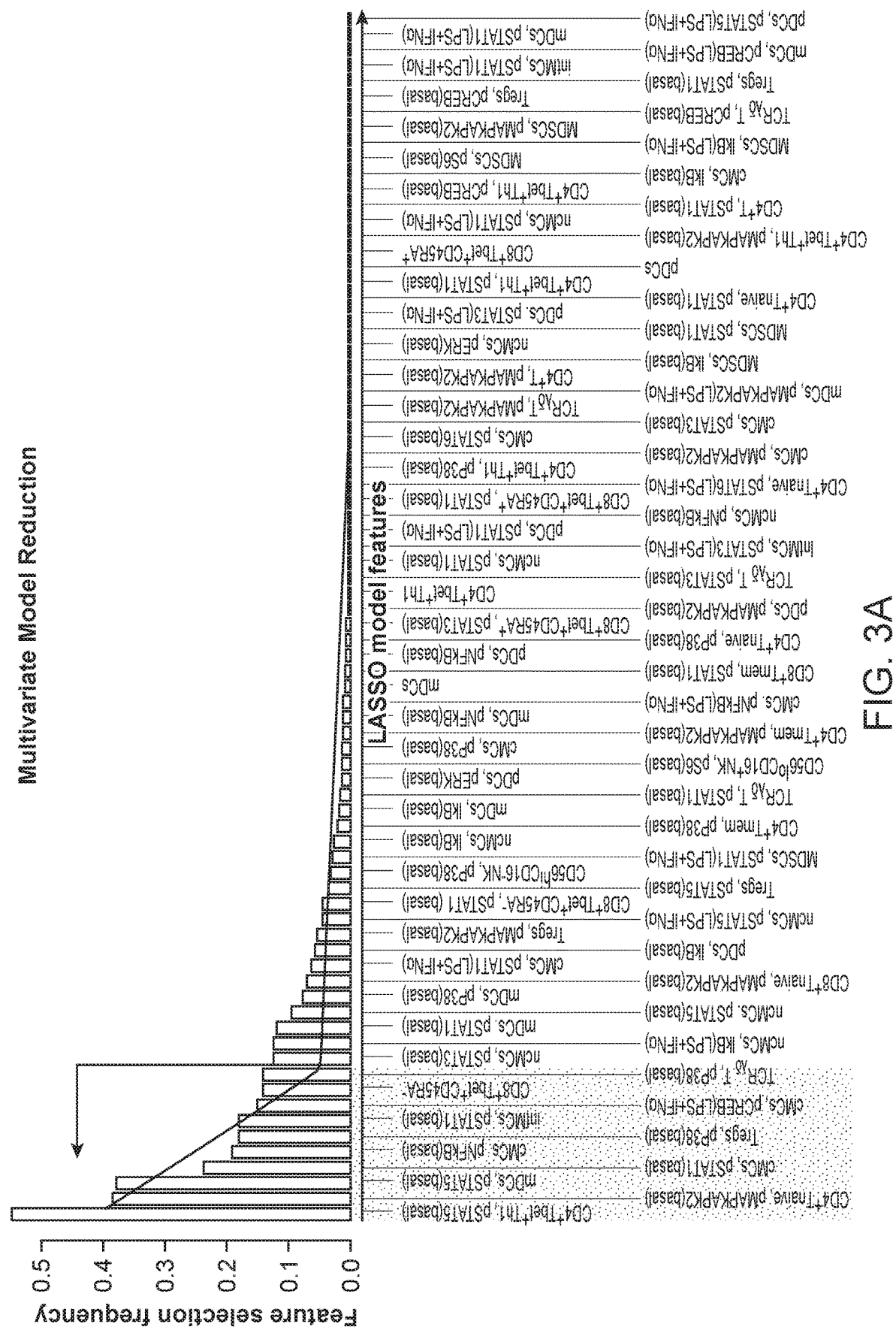
FIG. 3A-3B. Identification of the most informative features classifying patients who develop preeclampsia.

Pro-inflammatory immune responses early in pregnancy contribute to abnormal immune system dynamics in preeclampsia. The LASSO method allowed a system-level analysis of immune dysfunction in preeclampsia anchored by a statistically-stringent multivariate model. To highlight the most informative features of the multivariate model and facilitate biological interpretation, we applied a piecewise regression method that reduced the model to 10 components (FIG. 3A) that were highly discriminating between control and preeclamptic pregnancies: the median area under the curve (AUC) was 0.90, within an IQR of 0.81 to 0.92. Most (90%) of the informative immune features were intracellular signaling responses (AUC 0.80-0.92), while the cell frequency features had a much weaker predictive performance for preeclampsia (AUC=0.65). Eight out of these ten immune features remained highly significant as predictors of preeclampsia after controlling for demographic and clinical variables (BMI, presence of autoimmune disease, hypertension, and type 2 diabetes) in a multivariate linear regression analysis (Table 1).

TABLE 1

| Features | Selection frequency | p-value | AUC | Community | p-value (adjusted for clinical covariates) |
| --- | --- | --- | --- | --- | --- |
| pSTAT5 (basal), CD4$_+$Tbet$_+$Th1 | 0.5483 | 0.0001 | 0.9167 | 2 | 0.001 |
| MAPKAPK2 (basal), CD4$_+$Tnaive | 0.3879 | 0.0032 | 0.9091 | 6 | 0.014 |
| pSTAT5 (basal), mDCs | 0.3798 | 0.0026 | 0.9167 | 4 | 0.003 |
| pSTAT1 (basal), cMCs | 0.2379 | 0.0117 | 0.7955 | 4 | <0.001 |
| pNFkB (basal), cMCs | 0.1916 | 0.0040 | 0.8182 | 13 | 0.005 |
| pP38 (basal), Tregs | 0.1828 | 0.0323 | 0.8182 | 14 | 0.044 |
| pSTAT1 (basal), intMCs | 0.1796 | 0.0004 | 0.9318 | 4 | 0.001 |
| pCREB (LPS + IFN-$\alpha$), cMCs | 0.1510 | 0.0177 | 0.7955 | 10 | 0.259 |
| CD8$_+$Tbet$_+$CD45RA$_-$, frequency | 0.1435 | 0.1137 | 0.6591 | N/A | 0.755 |
| pP38 (basal), TCR$_{\gamma\delta}$ T | 0.1415 | 0.0002 | 0.9015 | 1 | <0.001 |

Table 1. Reduced LASSO model components. As BMI, autoimmune disease, hypertension, type 2 diabetes were significantly different between the two study groups, a multiple linear regression was performed to determine whether the presence of preeclampsia was still an independent predictor of the components of the reduced LASSO model after accounting for these potential clinical confounders. Results showed that the presence of preeclampsia was still a significant predictor for eight out of ten model components after adjusting for BMI, autoimmune disease, hypertension, and type 2 diabetes. Preeclampsia was not a significant predictor of the pCREB, cMCs, LPS + IFN-$\alpha$ and the CD8+Tbet+CD45RA− frequency model components after accounting for these confounding variables (p-value > 0.05, Mann-Whitney U test).

Figure 3B:
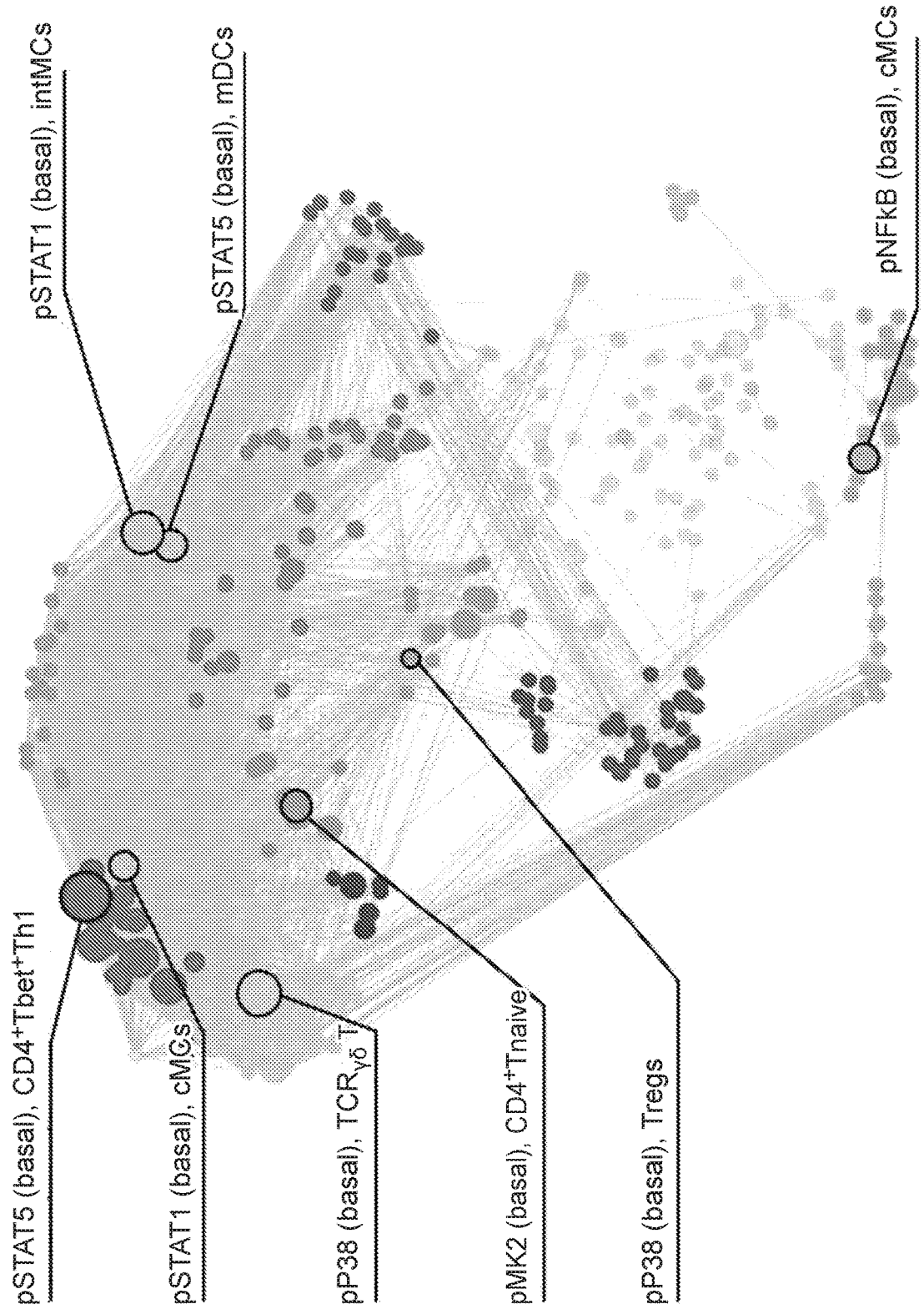
Figure 5:
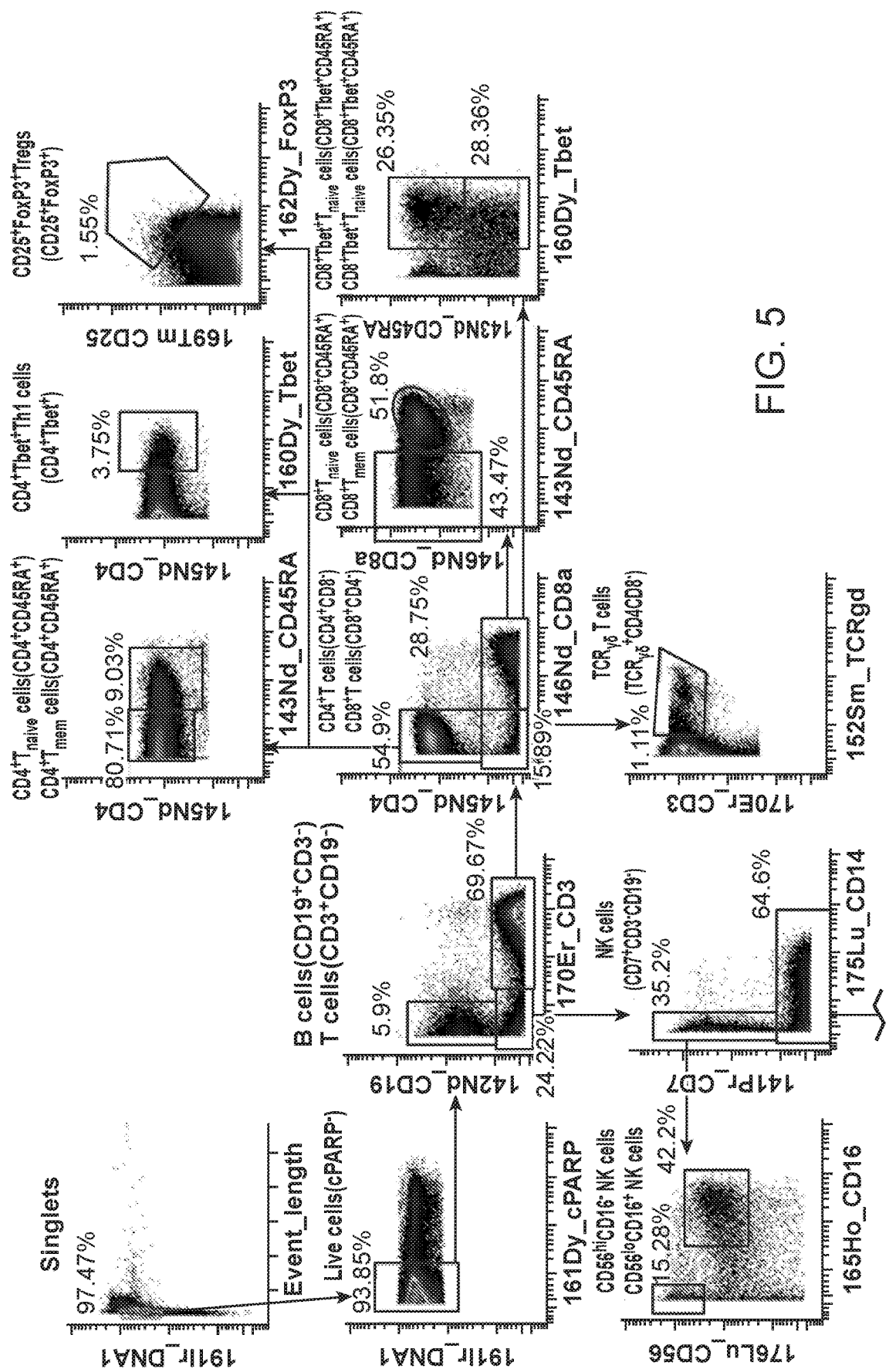
FIG. 5. Gating strategy. Twenty-one immune cell subsets were gates based on established guidelines for manual gating of innate and adaptive cells.
Figure 5:
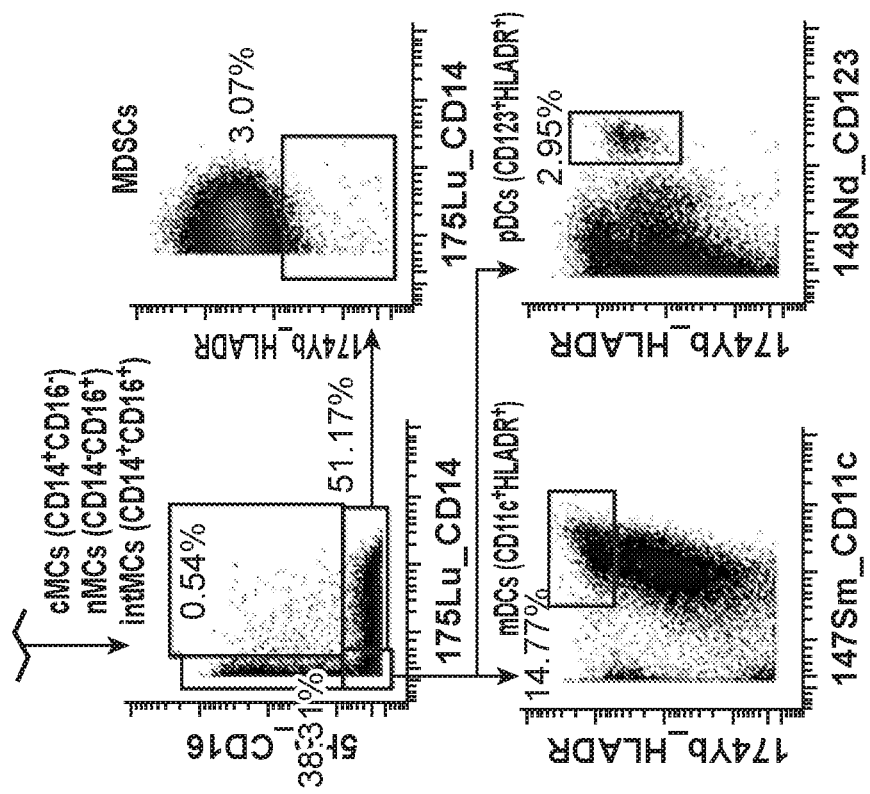

These eight informative immune features appeared within six of the 14 communities, consistent with dysregulated immune dynamics that spanned multiple immune compartments (FIG. 3B). The most informative feature was the pSTAT5 signal (basal) in CD4+Tbet+Th1 cells (AUC=0.92, p=8.0E-5, FIG. 4A). The pSTAT5 signal increased consistently in Th1 cells between the first and second trimesters in the control group, but decreased consistently in women who developed preeclampsia (FIG. 4A). Further examination of individual time points revealed that the pSTAT5 signal in Th1 cells was higher in women with preeclampsia compared with controls in the first trimester and then gradually decreased during the second trimester (FIG. 4A, inset). These results are consistent with the prevailing theory of the presence of a predominance of Th1 in preeclampsia, given that STAT5 can potentiate Th1 differentiation.

Because the JAK/STAT5 signaling pathway is implicated in multiple aspects of CD4+T cell differentiation, notably in the differentiation and stability of peripheral Tregs, we tested whether observed pSTAT5 dynamics were restricted only to Th1 cells. In Community 2 (defined by the STAT5 signaling response) the abnormal pSTAT5 dynamics were shared among several T cell subsets including CD4+ Tnaive cells and CD25+FoxP3+ Tregs (FIG. 8). The pSTAT5 signal in Tregs increased between the first and second trimesters in the control group, but did not change in the preeclamptic women. The results highlight an important role for STAT5-dependent responses across multiple CD4+T cell subsets that are disrupted prior to the clinical onset of preeclampsia.

The remaining immune features of the reduced model suggested that, overall, strong pro-inflammatory cell responses early during pregnancy altered the immunologic trajectory of women who went on to develop preeclampsia. In innate immune compartments, the pSTAT1, pSTAT5, and pNFκB signals (basal) were elevated in intermediate monocytes (intMCs) (AUC=0.93, p=4.0E-4), myeloid dendritic cells (mDCs) (AUC=0.92, p=0.0026), and classical monocytes (cMCs) (pSTAT1: AUC=0.90 p=4.1E-4; pNFκB: AUC=0.82, p=4.0E-3), respectively, during the first trimester in preeclamptic women compared with controls (FIG. 4B-E). These responses gradually decreased during preeclamptic pregnancies, but increased in the control group. In adaptive immune compartments, elevated pro-inflammatory signaling responses in Th1 cells (pSTAT5) during the first trimester of pregnancy were coupled with abnormal signaling dynamics in CD4+T naïve cells (pMAPKAPK2, AUC=0.91, p=3.2E-3), TCR$_{\gamma\delta}$ (pP38, AUC=0.9, p=2.0E-4) and CD25+FoxP3+Tregs (pP38, AUC=0.82, p=0.032) (FIG. 4F-H). Of note, the pP38 signal, which is required for Treg suppressive function, increased in Tregs during pregnancy in controls but not in women with preeclampsia.

We employed a high-parameter mass cytometry immunoassay for an in-depth assessment of the dynamics of the peripheral immune system during normal and preeclamptic pregnancies. Analysis of the high-dimensional immunological dataset identified immune system dysfunction detectable in the maternal blood 12 to 14 weeks before the clinical signs of preeclampsia were evident. Individual components of the multivariate model highlighted profound dysregulation of intracellular signaling dynamics that were strongly associated with the subsequent development of preeclampsia (median AUC 0.91, IQR [0.82, 0.92]).

High-parameter flow cytometry technologies such as mass cytometry have transformed the ability to profile the human immune system. However, the high dimensionality of the resulting data presents a major analytical challenge to conventional statistical analysis. Application of regularized regression algorithms (such as LASSO) combined with a cross-validation method to ensure generalizability of the model outputs provided a robust statistical solution to this analytic challenge. In this study, the LASSO analysis provided a statistically stringent multivariate model that distinguished healthy pregnancies from those with preeclampsia, while simultaneously assessing over 450 immune features. The performance of individual model components in stratifying women who develop preeclampsia was also remarkable. Using the AUC as a metric, the individual performances of the top five model components to predict preeclampsia were each above 0.9, which signifies excellent accuracy. These results may be due to several aspects of our analysis that differ from prior studies reporting on immunological biomarkers of preeclampsia. The functional interrogation of signaling responses, rather than cell distribution may have been more informative; the simultaneous survey of multiple innate and adaptive immune cell subsets allowed for agnostic identification of the most informative immune features; and the analysis, which focused on immune cell dynamics rather than static immunologic events, may have allowed a more sensitive detection of pregnancy-related immune dysfunctions.

The most informative features of our analysis were the basal pSTAT5 signals in $CD4^+T$ cell subsets (AUC=0.92, p=8.0E-5). Notably, the pSTAT5 signal in $CD4^+T$ cells was also the most informative component of a multivariate model predictive of the age of gestation in a prior study of normal pregnancy. These findings, derived from two independent studies, shows that assessing pSTAT5 dynamics in $CD4^+T$ cell subsets early in pregnancy provides a key element for diagnostic immunoassays predictive of preeclampsia.

The JAK/STAT5 pathway has been implicated in multiple, and seemingly conflicting, aspects of $CD4^+T$ cell development. Downstream of IL-2, in vivo and in vitro studies show that the IL-2/STAT5 pathway controls Th2 differentiation (by inducing the expression of the IL-4 receptor) as well as Th1 differentiation (by inducing the expression of Tbet and the IL-12 receptor). The IL-2/STAT5 pathway is also critical for promoting peripheral Tregs and inhibiting Th17 differentiation. Therefore, the decreasing pSTAT5 signal—which was higher during the first trimester in the preeclamptic group than in the control group—observed in $CD4^+T$ cell subsets early in preeclamptic pregnancies likely reflects multiple dysfunctional processes affecting T cell differentiation, including increased Th1 over Th2 differentiation during the first trimester as well as decreased Treg differentiation between the first and second trimesters.

However, IL-2 is not the only factor regulating the JAK/STAT5 signaling pathway. In fact, multiple inflammatory, but also hormonal, and placental factors implicated in pregnancy converge onto the JAK/STAT5 pathway, including prolactin, chorionic somatomammotropin hormone (CSH)-1, IFN-γ and IL-3. Leptin, which has consistently been associated with preeclampsia in multiple large-scale proteomics studies can also activate the JAK/STAT5 pathway. Assessment of JAK/STAT5 signaling dynamics may therefore provide a sensitive cellular readout of immune dysfunction that reflects the integration of multiple signals ultimately driving abnormal $CD4^+T$ cell responses early in the pathogenesis of preeclampsia.

Several other results of our analysis resonated well with prior knowledge of immune system dysfunction associated with preeclampsia, notably among innate immune cell subsets. In general, observed differences in the rate of change of innate immune responses (decelerated in the preeclampsia group compared to the control group) were driven in part by higher signaling responses during the first trimester of pregnancy in the preeclampsia group. In cMCs, the basal pNFκB signals was increased in the preeclampsia group in the first trimester compared to the control group (FIG. 4E). A similar finding was observed for the pSTAT1 signal in the pro-inflammatory intMCs monocyte subtype (FIG. 4C). These findings of elevated signaling tone in innate immune cells is consistent with previous studies suggesting exaggerated activation of proinflammatory innate immune responses in preeclampsia.

Interestingly, the majority of dysregulated immune responses were signaling responses rather than frequency changes. In this regard, some of our findings differ from previous analyses of peripheral immune responses associated with preeclampsia. For instance, neither the frequency of Tregs or of Th1 cells—which have previously been shown to differ between normal and preeclamptic pregnancies—were selected as informative features of the multivariate model. Instead, measurement over time of signaling responses in Tregs (pP38 and pSTAT5) and in $CD4^+Tbet^+$ Th1 cells (pSTAT5) were among the strongest individual classifiers for preeclampsia. These results show that a functional read-out of proximal signaling responses is more informative than the assessment of cell distribution alone in identifying immune dysfunction associated with preeclampsia.

Our study reveals a disruption of the dynamics of the maternal immune system that is detectable months before the clinical onset of preeclampsia. The data and analytical approaches provided here show that measures of maternal immune system dynamics early in pregnancy can provide for early prediction and prevention of preeclampsia.

Materials and Methods

Study design. We recruited study subjects from a cohort of 393 pregnant women who were prospectively examined for an array of environmental and biological factors associated with uncomplicated and pathological pregnancies. Pregnant women receiving routine antepartum care at the Lucile Packard Children's Hospital at Stanford University were eligible for the study if they were 18 years of age or older and in their first trimester of pregnancy. At least two blood samples were obtained during the first (7 to 14 weeks), second (15 to 20 weeks), and third (24 to 32 weeks) trimesters of pregnancy. An in-depth mass cytometry analysis or peripheral immune cells was performed on serial blood samples (two for each patient) collected in 11 women with preeclampsia (preeclampsia group) and 12 women with a normotensive pregnancy (control group). The diagnosis of preeclampsia was made (and verified by a senior obstetrician) according to the American College of Obstetricians and Gynecologists criteria, as a persistent systolic blood pressure (BP) of 140 mmHg or higher, or as a diastolic BP of 90 mmHg or higher after 20 weeks of GA in a woman with previously normal BP range along with one or more of the following: new-onset proteinuria, or in the absence of proteinuria, the presence of severe features such as new-onset thrombocytopenia, impaired liver function, renal insufficiency, pulmonary edema, or visual or cerebral disturbances. Early-onset preeclampsia was defined as preeclampsia developing before 34 weeks of gestation. Patients in the control group were selected if they had a normotensive pregnancy leading to the delivery of a healthy neonate at term (gestational age>37 weeks), and to ensure matching of gestational age at time of sampling with the preeclampsia group. One patient in the control group had well-managed gestational diabetes mellitus (GDM) with an otherwise uncomplicated pregnancy. The study was approved by the Institutional Review Board of Stanford University, and all participants signed an informed consent. Demographics and pregnancy characteristics for the 23 participants included in the analysis are summarized in Table 2. The study was sponsored by the March of Dimes Prematurity Research Center, which had no role in its design or interpretation.

Sample collection and PBMC stimulation. Blood samples were collected at indicated time points (FIG. 1) and peripheral blood mononuclear cells (PBMCs) were prepared and cryopreserved according to standard protocols. On the day of sample stimulation, PBMCs were thawed and rested in culture media containing 10% fetal bovine serum (Gibco) at 37° C. for 2 hours. PBMCs were counted and checked for viability. Samples with less than 60% viability or less than $10^6$ cells were excluded. There was no difference in total cell count, live cell count, viability, and storage time at time point 1 or 2 between the two groups. PBMC samples were stimulated with either LPS (1 µg/mL) and IFN-α (100 ng/mL), or left unstimulated at 37° C. for 15 min, then fixed for further analysis with mass cytometry. The availability of PBMC samples allowed performing only one stimulation condition. To maximize the information obtained from stimulated samples, LPS (1 µg/mL) and IFN-α (100 ng/mL) were utilized together after ensuring that little overlap was detected in our immunoassay between immune signaling responses to LPS (restricted to pERK1/2, pP38, pMAPKAPK2, pS6, pCREB, pNF-κB in innate immune cells) and to IFN-α (restricted to pSTAT1, pSTAT3, pSTAT5, pSTAT6 in innate and adaptive immune cells) (FIG. 6).

Sample barcoding. To minimize the effect of experimental variability on mass cytometry measurements between samples from different time points and between samples from the control and preeclampsia groups, samples corresponding from the entire time series collected from one woman with preeclampsia and one control matched for GA at time of sampling were barcoded, pooled, stained and run simultaneously on the mass cytometry instrument.

Antibody staining and mass cytometry. The mass cytometry antibody panel included 22 antibodies that were used for phenotyping of immune cell subsets and 11 antibodies for the functional characterization of immune cell responses (Table 2). Antibodies were either obtained pre-conjugated (Fluidigm, Inc.) or were obtained as purified, carrier-free (no BSA, gelatin) versions, which were then conjugated in-house with trivalent metal isotopes utilizing the MaxPAR antibody conjugation kit (Fluidigm, Inc.). After incubation with Fc block (Biolegend), pooled barcoded cells were stained with surface antibodies then permeabilized with methanol and stained with intracellular antibodies. All antibodies used in the analysis were titrated and validated on samples that were processed identically to the samples used in the study. Barcoded and antibody-stained cells were analyzed on a Helios mass cytometer (Fluidigm, Inc.).

Derivation of immune features. The mass cytometry data was normalized using Normalizer v0.1 MATLAB Compiler Runtime (MathWorks). Files were then de-barcoded with a single-cell MATLAB de-barcoding tool. Manual gating was performed using CellEngine (Primity Bio, Fremont, CA) according to our previous gating strategy (26). The following 21 cell types were included in the analysis: B cells, Natural Killer cells (NK), $CD56^{hi}CD16^-$ NK cells, $CD56^{lo}CD16^+$ NK cells, $CD4^+$T cells, $CD4^+CD45RA^-$T cells ($CD4^+$Tmem), $CD4^+CD45RA^+$T cells ($CD4^+$Tnaive), $CD4^+Tbet^+$T cells (Th1), $CD25^+FoxP3^+CD4^+$T cells (Tregs), $CD8^+$T cells, $CD8^+CD45RA^-$T cells ($CD8^+$Tmem), $CD8^+CD45RA^+$T cells ($CD8^+$Tnaive), $CD8^+Tbet^+$ $CD45RA^-$ cells, $CD8^+Tbet^+CD45RA^+$T cells, $TCR_{\gamma\delta}$T cells, $CD14^+CD16^-$ classical monocytes (cMCs), $CD14^-CD16^+$ non-classical MCs (ncMCs), $CD14^+CD16^+$ intermediate MCs (intMCs), monocytic myeloid-derived suppressor cells (M-MDSCs), myeloid dendritic cells (mDCs), and plasmacytoid dendritic cells (pDCs).

Cell frequency features: Cell frequencies were expressed as a percentage of gated singlet live mononuclear cells ($cPARP^-CD45^+CD66^-$).

Basal signaling immune features: Basal intracellular signaling activities were derived from the analysis of unstimulated samples. The phospho-signal intensity of the following functional markers was simultaneously quantified per single cells: pSTAT1, pSTAT3, pSTAT5, pSTAT6, pNFκB, pMAPKAPK2, pP38, prpS6, pERK1/2, pCREB. Total IκB was measured to assess IκB degradation. For each cell type, signaling immune features were calculated as the mean signal intensity (arcsinh transformed value) of each signaling protein.

Intracellular signaling response features: For each cell type, the arcsinh difference (arcsinh ratio) in signal intensity between the stimulated and unstimulated conditions was calculated for each functional marker.

Parametrization of immune feature dynamics. Parametrization of immune feature dynamics: For each immune feature, the rate of change between the two sampling time points was estimated as:

$$\rho = \frac{\text{immune feature}_{T2} - \text{immune feature}_{T1}}{GA_{T2} - GA_{T1}}$$

Statistical analyses. A multivariate LASSO (least absolute shrinkage and selection operator) linear logistic regression method was utilized for this study. LASSO uses a $L_1$ penalization over the classifier's coefficients to develop a "sparse" model, which facilitates interpretability, downstream validation, and reproducibility in resource-limited settings. The feature matrix was constructed using the rate of change of immune feature (ρ) as follows:

For a design matrix P of immune feature rates (ρ), and a binary response vector of preeclampsia Y, a multivariate linear logistic LASSO regression model was developed to calculate the coefficients β for each entity in P to maximize the overall log-likelihood using the conditional likelihood of C given P, $$l(\beta) = \sum_{i=1}^{n} \log p_{yi}(\rho_i \beta)$$

where $$p_{yi}(\rho_i;\beta) = Pr(C = y_i | P = \rho_i; \beta)$$

With this convention, log-likelihood can be rewritten as $$l(\beta) = \sum_{i=1}^{n} [y_i \beta^T \rho_i - \log(1 + \exp(\beta^T \rho_i))]$$

An $L_1$ regularization was applied on the β coefficient to reduce the model complexity, such that $$l(\beta) = \sum_{i=1}^{n} [y_i \beta^T \rho_i - \log(1 + \exp(\beta^T \rho_i))] + \lambda \sum_{j=1}^{p} |\beta_j|$$

where lambda $\lambda$ is selected by cross-validation. This produces a sparse model in which only a limited number of features are used.

The model was trained on 20 randomly-selected patients and tested on the remaining three. After 100 iterations, the mean of all predictions for a given patient in the test set was used as the final blinded prediction. This strategy minimizes the risk of overfitting by ensuring the models are always tested on samples that were not previously seen by the algorithm.

Model reduction: The relative weights of immune features selected by the LASSO method were determined using the frequency at which individual immune feature were selected through all cross-validation iterations. The top ten features were chosen by a piecewise regression model, a statistical technique used to specify an abrupt shift over the response variable corresponding to the explanatory variable. We used student t test to compare individual immune features between control and preeclampsia groups if the data is normal distributed test by Shapiro-Wilk test, otherwise, a Mann-Whitney nonparametric test was used.

Confounder analysis. We analyzed 14 demographic and comorbid conditions, including age, race, ethnicity, Body Mass Index (BMI), GA at delivery, total number of pregnancies, multiplicity, parity, gestational diabetes, type 2 diabetes, preeclampsia history, autoimmune disease, and chronic hypertension. Women with preeclampsia had higher BMI (p=2.0E-3) than the Controls (student t test). Higher rates of type 2 diabetes (p=4.5E-2), chronic hypertension (p=4.5E-2) and autoimmune diseases (p=8.0E-3) were found in the patients with preeclampsia, which were significant by Fisher's exact test. Confounder analysis was performed using SPSS version 12.0 (SPSS Inc., Chicago, IL, USA).

Correlation network. Spearman correlation analyses were performed between pairs of immune features measured at each time point. The graphical representation of the correlation network shows edges for significant correlations between data pairs (p<1.0E-12). Edge length is proportional to $-\log 10$ (p-value). The graph layout was calculated using the t-SNE algorithm and visualized using the i-graph R package.

TABLE 2

|  | Control (n = 12) | Preeclampsia (n = 11) |
|---|---|---|
| Demographics |  |  |
| Age (years, mean ± SD) | 33.4 ± 4.7 | 30.6 ± 5.4 |
| BMI (kg/m$^2$, mean ± SD) | 24.5 ± 5.6 | 29.4 ± 4.6 * |
| BMI at delivery (kg/m$^2$, mean ± SD) | 28.2 ± 4.7 | 33.4 ± 4.5 * |
| GA at delivery (weeks, mean ± SD) | 39.3 ± 1.2 | 37.6 ± 3.0 |
| Gravida (mean ± SD) | 3.0 ± 1.5 | 2.5 ± 2.5 |
| Para (mean ± SD) | 1.5 ± 1.5 | 0.7 ± 1.5 |
| Twin pregnancy | 0 | 1 |
| Race/ethnicity |  |  |
| Asian | 0 | 3 |
| Black | 0 | 1 |
| White | 10 | 4 |
| Other | 2 | 3 |
| Hispanic | 3 | 3 |
| Non-hispanic | 9 | 8 |
| Mode of delivery |  |  |
| Normal spontaneous vaginal delivery | 8 | 5 |
| Cesarean delivery | 4 | 6 |
| Preeclampsia characteristics |  |  |
| Preeclampsia with severe feature |  | 7 |
| Early-onset preeclampsia |  | 2 |
| Comorbidity |  |  |
| Gestational diabetes | 1 | 1 |
| Type II diabetes | 0 | 2 |
| Autoimmune disease | 0 | 3 |
| Chrome hypertension | 0 | 2 |

* $p < 0.05$, by using unpaired student t test

TABLE 2

| Antibody | Manufacturer | Symbol | Mass | Clone | Comment |
|---|---|---|---|---|---|
| Barcode 1 | Trace Sciences | Pd | 102 |  | Barcode |
| Barcode 2 | Trace Sciences | Pd | 104 |  | Barcode |
| Barcode 3 | Trace Sciences | Pd | 105 |  | Barcode |
| Barcode 4 | Trace Sciences | Pd | 106 |  | Barcode |
| Barcode 5 | Trace Sciences | Pd | 108 |  | Barcode |
| Barcode 6 | Trace Sciences | Pd | 110 |  | Barcode |
| CD235ab | Biolegend | In | 113 | HIR2 | Phenotype |
| CD61 | BD | In | 113 | VI-PL2 | Phenotype |
| CD45 | Biolegend | In | 115 | HI30 | Phenotype |
| CD66 | BD | La | 139 | CD66a-B1.1 | Phenotype |
| CD7 | BD | Pr | 141 | M-T701 | Phenotype |
| CD19 | Biolegend | Nd | 142 | HIB19 | Phenotype |
| CD45RA | Biolegend | Nd | 143 | HI100 | Phenotype |
| CD11b | Fluidigm | Nd | 144 | ICRF44 | Phenotype |
| CD4 | Fluidigm | Nd | 145 | RPA-T4 | Phenotype |
| CD8a | Fluidigm | Nd | 146 | RPA-T8 | Phenotype |
| CD11c | Fluidigm | Sm | 147 | Bu15 | Phenotype |
| CD123 | Biolegend | Nd | 148 | 6H6 | Phenotype |
| pCREB (pS133) | CST | Sm | 149 | 87G3 | Function |
| pSTAT5 (pY694) | Fluidigm | Nd | 150 | 47 | Function |
| pP38 (pT180/pY182) | BD | Eu | 151 | 36/p38 | Function |
| TCRγδ | Fluidigm | Sm | 152 | 11F2 | Phenotype |
| pSTAT1 (pY701) | Fluidigm | Eu | 153 | 58D6 | Function |
| pSTAT3 (pY705) | CST | Sm | 154 | M9C6 | Function |
| pS6 (pS235/pS236) | CST | Gd | 155 | D57.2.2E | Function |

TABLE 2-continued

| Antibody | Manufacturer | Symbol | Mass | Clone | Comment |
|---|---|---|---|---|---|
| CD33 | Fluidigm | Gd | 158 | WM53 | Phenotype |
| pMAPKAPK2 (pT334) | Fluidigm | Tb | 159 | 27B7 | Function |
| Tbet | Fluidigm | Gd | 160 | 4B10 | Phenotype |
| cPARP | BD | Dy | 161 | F21-852 | Function |
| FoxP3 | Fluidigm | Dy | 162 | PCH101 | Phenotype |
| IxB | Fluidigm | Dy | 164 | L35A5 | Function |
| CD16 | Fluidigm | Ho | 165 | 3G8 | Phenotype |
| pNFxB (pS529) | Fluidigm | Er | 166 | K10-895.12.50 | Function |
| PSTAT6 (PY641) | Fluidigm | Er | 168 | 18 | Function |
| CD25 | Biolegend | Tm | 169 | M-A251 | Phenotype |
| CD3 | Fluidigm | Er | 170 | UCHT1 | Phenotype |
| pERK1/2 (pT202/pY204) | Fluidigm | Yb | 171 | D13.14.4E | Function |
| HLA-DR | Fluidigm | Yb | 174 | L243 | Phenotype |
| CD14 | Fluidigm | Yb | 175 | M5E2 | Phenotype |
| CD56 | BD | Yb | 176 | NCAM16.2 | Phenotype |
| DNA1 | Fluidigm | Ir | 191 | | DNA |
| DNA2 | Fluidigm | Ir | 192 | | DNA |

1. O. American College of, Gynecologists, P. Task Force on Hypertension in, Hypertension in pregnancy. Report of the American College of Obstetricians and Gynecologists' Task Force on Hypertension in Pregnancy. *Obstet Gynecol* 122, 1122-1131 (2013).
2. E. A. Steegers, P. von Dadelszen, J. J. Duvekot, R. Pijnenborg, Pre-eclampsia. *Lancet* 376, 631-644 (2010).
3. T. Chaiworapongsa, P. Chaemsaithong, S. J. Korzeniewski, L. Yeo, R. Romero, Pre-eclampsia part 2: prediction, prevention and management. *Nature reviews. Nephrology* 10, 531-540 (2014).
4. C. W. Redman, I. L. Sargent, Latest advances in understanding preeclampsia. *Science* 308, 1592-1594 (2005).
5. H. Zeisler, M. Hund, S. Verlohren, The sFlt-1:PlGF Ratio in Women with Suspected Preeclampsia. *N Engl J Med* 374, 1785-1786 (2016).
6. D. J. Freeman et al., Short- and long-term changes in plasma inflammatory markers associated with preeclampsia. *Hypertension* 44, 708-714 (2004).
7. C. W. Redman, I. L. Sargent, Immunology of pre-eclampsia. *Am J Reprod Immunol* 63, 534-543 (2010).
8. E. Laresgoiti-Servitje, A leading role for the immune system in the pathophysiology of preeclampsia. *Journal of leukocyte biology* 94, 247-257 (2013).
9. T. Chaiworapongsa, P. Chaemsaithong, L. Yeo, R. Romero, Pre-eclampsia part 1: current understanding of its pathophysiology. *Nature reviews. Nephrology* 10, 466-480 (2014).
10. P. C. Arck, K. Hecher, Fetomaternal immune cross-talk and its consequences for maternal and offspring's health. *Nature medicine* 19, 548-556 (2013).
11. M. PrabhuDas et al., Immune mechanisms at the maternal-fetal interface: perspectives and challenges. *Nat Immunol* 16, 328-334 (2015).
12. S. Saito, A. Shiozaki, A. Nakashima, M. Sakai, Y. Sasaki, The role of the immune system in preeclampsia. *Molecular aspects of medicine* 28, 192-209 (2007).
13. D. Darmochwal-Kolarz et al., The predominance of Th17 lymphocytes and decreased number and function of Treg cells in preeclampsia. *J Reprod Immunol* 93, 75-81 (2012).
14. A. Steinborn et al., Pregnancy-associated diseases are characterized by the composition of the systemic regulatory T cell (Treg) pool with distinct subsets of Tregs. *Clin Exp Immunol* 167, 84-98 (2012).
15. N. G. Than et al., Integrated Systems Biology Approach Identifies Novel Maternal and Placental Pathways of Preeclampsia. *Front Immunol* 9, 1661 (2018).
16. M. Kashanian, F. Aghbali, N. Mahali, Evaluation of the diagnostic value of the first-trimester maternal serum high-sensitivity C-reactive protein level for prediction of pre-eclampsia. *The journal of obstetrics and gynaecology research* 39, 1549-1554 (2013).
17. L. H. Tangeras et al., Distinct First Trimester Cytokine Profiles for Gestational Hypertension and Preeclampsia. *Arteriosclerosis, thrombosis, and vascular biology* 35, 2478-2485 (2015).
18. M. D. Salazar Garcia et al., Early pregnancy immune biomarkers in peripheral blood may predict preeclampsia. *J Reprod Immunol* 125, 25-31 (2018).
19. D. Raymond, E. Peterson, A critical review of early-onset and late-onset preeclampsia. *Obstet Gynecol Surv* 66, 497-506 (2011).
20. J. A. Bastek, M. A. Elovitz, The role and challenges of biomarkers in spontaneous preterm birth and preeclampsia. *Fertil Steril* 99, 1117-1123 (2013).
21. S. C. Bendall et al., Single-cell mass cytometry of differential immune and drug responses across a human hematopoietic continuum. *Science* 332, 687-696 (2011).
22. M. H. Spitzer, G. P. Nolan, Mass Cytometry: Single Cells, Many Features. *Cell* 165, 780-791 (2016).
23. A. Olin et al., Stereotypic Immune System Development in Newborn Children. *Cell* 1174, 1277-1292 e1214 (2018).
24. Z. Good et al., Single-cell developmental classification of B cell precursor acute lymphoblastic leukemia at diagnosis reveals predictors of relapse. *Nature medicine* 24, 474-483 (2018).
25. Y. Simoni, M. H. Y. Chng, S. Li, M. Fehlings, E. W. Newell, Mass cytometry: a powerful tool for dissecting the immune landscape. *Curr Opin Immunol* 51, 187-196 (2018).
26. N. Aghaeepour et al., An immune clock of human pregnancy. *Sci Immunol* 2, (2017).
27. M. Le Gars et al., Increased Proinflammatory Responses of Monocytes and Plasmacytoid Dendritic Cells to Influenza A Virus Infection During Pregnancy. *J Infect Dis* 214, 1666-1671 (2016).
28. M. G. Ruocco, G. Chaouat, L. Florez, A. Bensussan, D. Klatzmann, Regulatory T-cells in pregnancy: historical perspective, state of the art, and burning questions. *Front Immunol* 5, 389 (2014).
29. A. W. Kay et al., Enhanced natural killer-cell and T-cell responses to influenza A virus during pregnancy. *Proceed-* ings of the National Academy of Sciences of the United States of America 111, 14506-14511 (2014).
30. D. A. Somerset, Y. Zheng, M. D. Kilby, D. M. Sansom, M. T. Drayson, Normal human pregnancy is associated with an elevation in the immune suppressive CD25$^+$ CD4$^+$ regulatory T-cell subset. *Immunology* 112, 38-43 (2004).
31. T. Pradeu, S. Jaeger, E. Vivier, The speed of change: towards a discontinuity theory of immunity? *Nat Rev Immunol* 13, 764-769 (2013).
32. R. Tibshirani, Regression Shrinkage and Selection via the Lasso. *Journal of the Royal Statistical Society. Series B (Methodological)* 58, 267-288 (1996).
33. S. Saito, M. Sakai, Th1/Th2 balance in preeclampsia. *J Reprod Immunol* 59, 161-173 (2003).
34. W. Liao, J. X. Lin, L. Wang, P. Li, W. J. Leonard, Modulation of cytokine receptors by IL-2 broadly regulates differentiation into helper T cell lineages. *Nat Immunol* 12, 551-U247 (2011).
35. M. A. Burchill, J. Y. Yang, C. Vogtenhuber, B. R. Blazar, M. A. Farrar, IL-2 receptor beta-dependent STAT5 activation is required for the development of Foxp3(+) regulatory T cells. *J Immuno* 1178, 280-290 (2007).
36. A. C. Cohen et al., Cutting edge: Decreased accumulation and regulatory function of CD4+ CD25(high) T cells in human STAT5b deficiency. *J Immunol* 177, 2770-2774 (2006).
37. L. Fainboim, L. Arruvito, Mechanisms involved in the expansion of Tregs during pregnancy: role of IL-2/STAT5 signalling. *J Reprod Immunol* 88, 93-98 (2011).
38. H. S. Adler et al., Activation of MAP kinase p38 is critical for the cell-cycle-controlled suppressor function of regulatory T cells. *Blood* 109, 4351-4359 (2007).
39. E. W. Newell, Y. Cheng, Mass cytometry: blessed with the curse of dimensionality. *Nat Immunol* 17, 890-895 (2016).
40. T. Hastie, R. Tibshirani, J. Friedman, *The elements of statistical learning: data mining, inference and prediction*. (Springer, ed. 2, 2009).
41. B. D. Taylor et al., First and second trimester immune biomarkers in preeclamptic and normotensive women. *Pregnancy Hypertens* 6, 388-393 (2016).
42. M. S. Ghaemi et al., Multiomics modeling of the immunome, transcriptome, microbiome, proteome and metabolome adaptations during human pregnancy. *Bioinformatics*, bty537-bty537 (2018).
43. J. Zhu, J. Cote-Sierra, L. Guo, W. E. Paul, Stat5 activation plays a critical role in Th2 differentiation. *Immunity* 19, 739-748 (2003).
44. A. Laurence et al., Interleukin-2 signaling via STAT5 constrains T helper 17 cell generation. *Immunity* 26, 371-381 (2007).
45. J. J. O'Shea, R. Plenge, JAK and STAT signaling molecules in immunoregulation and immune-mediated disease. *Immunity* 36, 542-550 (2012).
46. P. J. Murray, The JAK-STAT signaling pathway: input and output integration. *J Immunol* 178, 2623-2629 (2007).
47. Y. Gong et al., The long form of the leptin receptor regulates STAT5 and ribosomal protein S6 via alternate mechanisms. *The Journal of biological chemistry* 282, 31019-31027 (2007).
48. Y. M. Kim et al., Toll-like receptor 4: A potential link between "danger signals," the innate immune system, and preeclampsia? *Am J Obstet Gynecol* 193, 921.e921-921.e928 (2005).
49. P. Luppi et al., Preeclampsia activates circulating immune cells with engagement of the NF-kappaB pathway. *Am J Reprod Immunol* 56, 135-144 (2006).
50. P. H. Wise et al., Risky Business: Meeting the Structural Needs of Transdisciplinary Science. *The Journal of pediatrics* 191, 255-258 (2017).
51. N. Zivanovic, A. Jacobs, B. Bodenmiller, A practical guide to multiplexed mass cytometry. *Current topics in microbiology and immunology* 377, 95-109 (2014).
52. E. R. Zunder et al., Palladium-based mass tag cell barcoding with a doublet-filtering scheme and single-cell deconvolution algorithm. *Nature protocols* 10, 316-333 (2015).
53. R. Finck et al., Normalization of mass cytometry data with bead standards. *Cytometry. Part A: the journal of the International Society for Analytical Cytology* 83, 483-494 (2013).
54. L. van der Maaten, G. Hinton, Visualizing Data using t-SNE. *J Mach Learn Res* 9, 2579-2605 (2008).
55. H. T. Maecker, J. P. McCoy, R. Nussenblatt, Standardizing immunophenotyping for the Human Immunology Project. *Nat Rev Immunol* 12, 191-200 (2012).

What is claimed is:

1. A method for treating an individual having a propensity to develop preeclampsia during pregnancy, comprising:
obtaining a cellular biological sample for analysis comprising immune cells from a patient during pregnancy from at least two timepoints during the pregnancy, wherein the timepoints are in first trimester and second trimester;
measuring single cell basal levels of pSTAT5 in CD4$^+$ T cells in the biological sample at the at least two timepoints;
determining whether the single cell basal level of pSTAT5 in CD4$^+$ T cells has decreased between a first trimester sample and a second trimester sample during the pregnancy, indicating a propensity to develop preeclampsia; and
providing an assessment of the patient's prognosis for propensity to develop preeclampsia; and
treating the individual assessed as having a propensity to develop preeclampsia by administering aspirin or IL-2.

2. The method of claim 1, wherein the timepoints in first trimester and second trimester are from 12 to 15 weeks apart.

3. The method of claim 1, wherein the timepoint in first trimester is after about 11 gestational weeks.

4. The method of claim 1, wherein the timepoint in second trimester is prior to about 30 gestational weeks.

5. The method of claim 1, wherein the timepoint in first trimester is after about 11 gestational weeks and the timepoint in second trimester is prior to about 30 gestational weeks.

6. The method of claim 1, wherein the individual is treated by administration of a low dose of aspirin.

7. The method of claim 1, wherein the individual is treated by administration of a low dose of IL-2.

8. The method of claim 1, wherein the cellular biological sample is a blood sample.

9. The method of claim 1, wherein measuring single cell basal level of pSTAT5 is performed by mass cytometry immunoassay.

10. A method for treating an individual having a propensity to develop preeclampsia during pregnancy, comprising:
obtaining a cellular biological sample for analysis comprising immune cells from a patient during pregnancy from at least two timepoints during the pregnancy, wherein the timepoints are in first trimester and second trimester;

measuring single cell basal level of pSTAT5 in a subset of $CD4^+$ T cells at the at least two timepoints;

determining whether the single cell basal level of pSTAT5 in the subset of CD4+ T cells, has decreased between a first trimester sample and a second trimester sample during the pregnancy, indicating a propensity to develop preeclampsia; and providing an assessment of the patient's prognosis for propensity to develop preeclampsia; and treating the individual assessed as has having a propensity to develop preeclampsia by administering aspirin or IL-2.

11. The method of claim 10, wherein the subset of $CD4^+$ T cells is $CD4^+Tbet^+$T cells, $CD4^+CD45RA^+$ T cells, or $CD4^+CD25^+FoxP3^+$ Tregs.

12. The method of claim 10, wherein the timepoints in first trimester and second trimester are from 12 to 15 weeks apart.

13. The method of claim 10, wherein the timepoint in first trimester is after about 11 gestational weeks.

14. The method of claim 10, wherein the timepoint in second trimester is prior to about 30 gestational weeks.

15. The method of claim 10, wherein the timepoint in first trimester is after about 11 gestational weeks and the timepoint in second trimester is prior to about 30 gestational weeks.

16. The method of claim 10, wherein the individual is treated by administration of a low dose of aspirin.

17. The method of claim 10, wherein the individual is treated by administration of a low dose of IL-2.

18. The method of claim 10, wherein the cellular biological sample is a blood sample.

19. The method of claim 10, wherein measuring single cell basal level of pSTAT5 is performed by mass cytometry immunoassay.

* * * * *